United States Patent
Abel et al.

(10) Patent No.: US 7,122,727 B2
(45) Date of Patent: Oct. 17, 2006

(54) NUCLEIC ACID MOLECULES FROM WHEAT ENCODING AN R1-PROTEIN, AND TRANSGENIC PLANT CELLS AND PLANTS COMPRISING THE NUCLEIC ACID MOLECULES

(75) Inventors: Gernot Abel, Copenhagen (DK); Horst Lörz, Hamburg (DE); Stephanie Lütticke, Hamburg (DE); Ralf-Christian Schmidt, Potsdam (DE)

(73) Assignee: Bayer CropScience GmbH, Frankfurt (DE)

( * ) Notice: Subject to any disclaimer, the term of this patent is extended or adjusted under 35 U.S.C. 154(b) by 0 days.

(21) Appl. No.: 10/206,933

(22) Filed: Jul. 23, 2002

(65) Prior Publication Data

US 2003/0077805 A1    Apr. 24, 2003

Related U.S. Application Data

(62) Division of application No. 09/590,101, filed on Jun. 8, 2000, now Pat. No. 6,462,256.

(30) Foreign Application Priority Data

Jun. 11, 1999    (DE) ................. 199 26 771

(51) Int. Cl.
  C12N 5/04      (2006.01)
  C12N 15/82     (2006.01)
  A01H 5/00      (2006.01)
  A01H 5/10      (2006.01)
  C12P 19/04     (2006.01)
(52) U.S. Cl. .................... 800/320.3; 435/101; 435/410
(58) Field of Classification Search ................ 800/284, 800/285, 286, 298, 320.3; 435/419, 101
See application file for complete search history.

(56) References Cited

U.S. PATENT DOCUMENTS 6,462,256 B1    10/2002    Abel et al.

FOREIGN PATENT DOCUMENTS

| DE | 196 53 176 A1 | 6/1998 |
|---|---|---|
| WO | WO 97/11188 | 3/1997 |
| WO | WO 98/27212 | 8/1998 |
| WO | WO 99/53072 | 10/1999 |
| WO | WO 00/28052 | 5/2000 |

OTHER PUBLICATIONS

Tang et al, 1999, Plant Cell 11:177-189.*
Klann et al, 1996, Plant Physiol. 112:1321-1330.*
Colliver et al, 1997, Plant Mol. Biol. 35:509-522.*
Arndt et al, 1997, Genome 40:785-797.*
Lorberth et al, "Inhibition of a Starch-Granule-Bound Protein Leads to Modified Starch and Repression of Cold Sweetening", vol. 16, May 1998, pp. 473-477.
Database EMBL 'Online!, Accession No. C71741, Sep. 19, 1997; Sasaki, T., "Rice cDNA, Partial Sequence (E0169_1A)", also referred to as XP002111458.
Rahman et al, "The Major Proteins of Wheat Endosperm Starch Granules", Aust. J. Plant Physiol, 1995, 22, 793-803.
Sijen and Kooter "Post-transcriptional gene-silencing: RNAs on the attack or on the defense?" *BioEssays* 22: 520-531.
Trevanion et al. "NADP-Malate Dehydrogenase in the $C_4$ Plant *Flaveria bidentis.*" *Plant Physiol.* 113: 1153-1165.
Faske et al. "Transgenic Tobacco Plants Expressing Pea Choloplast Nmdh cDNA in Sense and Antisense Orientation." *Plant Phyisol.* 115: 705-715.
Bowie, J. U. et al., "Deciphering the Message in Protein Sequences: Tolerance to Amino Acid Substitutions." 1990, Science, vol. 247, pp. 1306-1310.
Broun, P. et al., "Catalytic Plasticity of Fatty Acid Modification Enzymes Underlying Chemical Diversity of Plant Lipids." 1998, Science, vol. 282, pp. 1315-1317.
Cheng, M. et al., "Genetic Transformation of Wheat Mediated by *Agrobacterium tumefaciens*." 1997, Plant Physiol., vol. 115, pp. 971-980.
Hill, M. A. and Preiss, J. "Functional Analysis of Conserved Histidines in ADP-Glucose Pyrophosphorylase from *Escherichia coli*." 1998, Biochemical and Biophysical Research Communications, vol. 244, pp. 573-577.
Kossmann, J. et al., "Transgenic plants as a tool to understand starch biosynthesis." 1995, Progress in Biotechnol., vol. 10, pp. 271-278.
Lazar, E. et al., "Transforming Growth Factor a: Mutation of Aspartic Acid 47 and Leucine 48 Results in Different Biological Activities," 1988, Molecular and Cellular Biology, vol. 8, pp. 1247-1252.
Sonnewald, U. et al., "A second L-type isozyme of potato glucan phosphorylase: cloning, antisense inhibition and expression analysis." 1995, Plant Molecular Biology, vol. 27, pp. 567-576.
Sweetlove, L. J. et al., "Starch metabolism in tubers of transgenic potato (*Solanum tuberosum*) with increased ADPglucose pyrophosphorylase." 1996, Biochem. J., vol. 320, pp. 493-498.

* cited by examiner

Primary Examiner—Anne Kubelik
(74) Attorney, Agent, or Firm—Hunton & Williams LLP

(57) ABSTRACT

Nucleic acid molecules encoding an R1-protein from wheat are provided. Also provided are transgenic plant cells and plants containing the nucleic acid molecules, and starch obtainable from the transgenic plant cells and plants.

10 Claims, No Drawings

SEQUENCE LISTING

```
<160> NUMBER OF SEQ ID NOS: 10

<210> SEQ ID NO 1
<211> LENGTH: 672
<212> TYPE: DNA
<213> ORGANISM: Triticum aestivum
<220> FEATURE:
<221> NAME/KEY: CDS
<222> LOCATION: (3)..(449)

<400> SEQUENCE: 1 ct gaa gtg gtg aaa gga ctt gga gag aca ctt gtg gga gct tat cct        47
   Glu Val Val Lys Gly Leu Gly Glu Thr Leu Val Gly Ala Tyr Pro
   1               5                   10                  15 ggc cgt gcc atg agc ttc gtg tgt aag aaa gat gac ctt gac tct ccc        95
Gly Arg Ala Met Ser Phe Val Cys Lys Lys Asp Asp Leu Asp Ser Pro
                20                  25                  30 aag gta ctg ggt tac cct agc aag cca att ggt ctc ttc ata aag cgg       143
Lys Val Leu Gly Tyr Pro Ser Lys Pro Ile Gly Leu Phe Ile Lys Arg
            35                  40                  45 tca atc atc ttc cgc tca gac tct aat ggt gag gat ctg gaa ggt tac       191
Ser Ile Ile Phe Arg Ser Asp Ser Asn Gly Glu Asp Leu Glu Gly Tyr
         50                  55                  60 gct gga gca ggg ctg tat gat agt gtc cct atg gat gtg gaa gat gaa       239
Ala Gly Ala Gly Leu Tyr Asp Ser Val Pro Met Asp Val Glu Asp Glu
 65                  70                  75 gtt gta ctc gac tac acg acc gac cct ctc atc act gac tct gga ttc       287
Val Val Leu Asp Tyr Thr Thr Asp Pro Leu Ile Thr Asp Ser Gly Phe
 80                  85                  90                  95 cgg aac tca atc ctc tca agc att gca cgg gct ggc cac gcc atc gag       335
Arg Asn Ser Ile Leu Ser Ser Ile Ala Arg Ala Gly His Ala Ile Glu
                100                 105                 110 gag ctc tat ggg tca cca cag gat gtt gag gga gta gtg aag gat ggg       383
Glu Leu Tyr Gly Ser Pro Gln Asp Val Glu Gly Val Val Lys Asp Gly
            115                 120                 125
```

```
aag atc tac gta gtc cag aca tac cac aga tgt aat atg tat gta tac      431
Lys Ile Tyr Val Val Gln Thr Tyr His Arg Cys Asn Met Tyr Val Tyr
        130                 135                 140 gcg gct caa gtt gta gag tagtaggata tatggtcctt gctggcatgt              479
Ala Ala Gln Val Val Glu
    145 atagttgtac tcataggtgc acaacacatc tacgttgtta tttatttgca tatacgctca     539 gaataagctt tgatcacata ctgtatttcc tagagtacca gaaagtgtat gtacgatcag     599 gaatatgacc ttattaaaac cattgagggg aaatgttttg acttttgagc aatctaaaaa     659 aaaaaaaaaa aaa                                                        672

<210> SEQ ID NO 2
<211> LENGTH: 149
<212> TYPE: PRT
<213> ORGANISM: Triticum aestivum

<400> SEQUENCE: 2

Glu Val Val Lys Gly Leu Gly Glu Thr Leu Val Gly Ala Tyr Pro Gly
1               5                   10                  15

Arg Ala Met Ser Phe Val Cys Lys Lys Asp Asp Leu Asp Ser Pro Lys
            20                  25                  30

Val Leu Gly Tyr Pro Ser Lys Pro Ile Gly Leu Phe Ile Lys Arg Ser
        35                  40                  45

Ile Ile Phe Arg Ser Asp Ser Asn Gly Glu Asp Leu Glu Gly Tyr Ala
    50                  55                  60

Gly Ala Gly Leu Tyr Asp Ser Val Pro Met Asp Val Glu Asp Glu Val
65                  70                  75                  80

Val Leu Asp Tyr Thr Thr Asp Pro Leu Ile Thr Asp Ser Gly Phe Arg
                85                  90                  95

Asn Ser Ile Leu Ser Ser Ile Ala Arg Ala Gly His Ala Ile Glu Glu
            100                 105                 110

Leu Tyr Gly Ser Pro Gln Asp Val Glu Gly Val Val Lys Asp Gly Lys
        115                 120                 125

Ile Tyr Val Val Gln Thr Tyr His Arg Cys Asn Met Tyr Val Tyr Ala
    130                 135                 140

Ala Gln Val Val Glu
145

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
tattggaagc tcgagttgaa c                                               21

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
ttgagctgtc taatagatgc a                                               21
```

```
<210> SEQ ID NO 5
<211> LENGTH: 17
<212> TYPE: DNA
<213> ORGANISM: Artificial Sequence
<220> FEATURE:
<223> OTHER INFORMATION: primer

<400> SEQUENCE: 5
ctgtggtatg tctggac                                                          17

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
gaggaagcaa ggaaggaact gcag                                                  24

<210> SEQ ID NO 7
<211> LENGTH: 3418
<212> TYPE: DNA
<213> ORGANISM: Triticum aestivum
<220> FEATURE:
<221> NAME/KEY: CDS
<222> LOCATION: (3)..(3416)

<400> SEQUENCE: 7
```

| | | | | | | | | | | | | | | | | |
|---|---|---|---|---|---|---|---|---|---|---|---|---|---|---|---|---|
| ga | gga | aga | agg | aag | gaa | ctg | cag | gct | gag | ttg | gat | aat | gga | gcc | tca | 47 |
|    | Gly | Arg | Arg | Lys | Glu | Leu | Gln | Ala | Glu | Leu | Asp | Asn | Gly | Ala | Ser | |
|    | 1   |     |     | 5   |     |     |     |     | 10  |     |     |     |     | 15  |     | |
| gtt | gat | caa | tta | agg | aag | aaa | att | gtg | aaa | gga | aac | ctt | gaa | aag | aaa | 95 |
| Val | Asp | Gln | Leu | Arg | Lys | Lys | Ile | Val | Lys | Gly | Asn | Leu | Glu | Lys | Lys | |
|     |     |     | 20  |     |     |     |     | 25  |     |     |     |     | 30  |     |     | |
| gtt | tcc | aag | caa | ctg | gag | aag | aag | aag | tac | ttc | tca | gta | gaa | agg | att | 143 |
| Val | Ser | Lys | Gln | Leu | Glu | Lys | Lys | Lys | Tyr | Phe | Ser | Val | Glu | Arg | Ile | |
|     |     | 35  |     |     |     |     | 40  |     |     |     |     | 45  |     |     |     | |
| cag | cgc | aga | aac | aga | gat | atc | acg | caa | ctt | ctt | aat | aaa | cat | aag | cct | 191 |
| Gln | Arg | Arg | Asn | Arg | Asp | Ile | Thr | Gln | Leu | Leu | Asn | Lys | His | Lys | Pro | |
|     | 50  |     |     |     |     | 55  |     |     |     |     | 60  |     |     |     |     | |
| gtg | gtt | aca | gaa | cag | caa | gta | aaa | gct | gca | ccc | aaa | cag | cca | act | gtt | 239 |
| Val | Val | Thr | Glu | Gln | Gln | Val | Lys | Ala | Ala | Pro | Lys | Gln | Pro | Thr | Val | |
| 65  |     |     |     |     | 70  |     |     |     |     | 75  |     |     |     |     |     | |
| ttg | gat | ctc | ttc | aca | aag | tcc | ttg | caa | gag | ggg | gat | aac | tgt | gac | gtc | 287 |
| Leu | Asp | Leu | Phe | Thr | Lys | Ser | Leu | Gln | Glu | Gly | Asp | Asn | Cys | Asp | Val | |
| 80  |     |     |     |     | 85  |     |     |     |     | 90  |     |     |     |     | 95  | |
| cta | agc | agg | aag | ctt | ttc | aag | atc | ggt | gat | gag | gag | ata | ctg | gca | att | 335 |
| Leu | Ser | Arg | Lys | Leu | Phe | Lys | Ile | Gly | Asp | Glu | Glu | Ile | Leu | Ala | Ile | |
|     |     |     |     | 100 |     |     |     |     | 105 |     |     |     |     | 110 |     | |
| gcc | aca | aat | gct | cta | ggt | aaa | acc | aga | gtt | cac | ttg | gca | aca | aac | cgt | 383 |
| Ala | Thr | Asn | Ala | Leu | Gly | Lys | Thr | Arg | Val | His | Leu | Ala | Thr | Asn | Arg | |
|     |     | 115 |     |     |     |     | 120 |     |     |     |     | 125 |     |     |     | |
| atg | gag | cca | ctt | att | ctt | cac | tgg | gca | ctg | gca | aaa | aat | ccc | gga | gaa | 431 |
| Met | Glu | Pro | Leu | Ile | Leu | His | Trp | Ala | Leu | Ala | Lys | Asn | Pro | Gly | Glu | |
|     | 130 |     |     |     |     | 135 |     |     |     |     | 140 |     |     |     |     | |
| tgg | gag | gca | cct | cct | tct | agc | ata | gtg | cct | tct | ggc | tca | aca | gtt | ctc | 479 |
| Trp | Glu | Ala | Pro | Pro | Ser | Ser | Ile | Val | Pro | Ser | Gly | Ser | Thr | Val | Leu | |
| 145 |     |     |     |     | 150 |     |     |     |     | 155 |     |     |     |     |     | |
| gac | aag | gca | tgt | gaa | act | tca | ttc | ggt | gag | tct | gaa | ttg | gat | ggt | ttg | 527 |
| Asp | Lys | Ala | Cys | Glu | Thr | Ser | Phe | Gly | Glu | Ser | Glu | Leu | Asp | Gly | Leu | |
| 160 |     |     |     |     | 165 |     |     |     |     | 170 |     |     |     |     | 175 | |
| caa | tac | cag | gtt | gtt | gag | ata | gag | ctt | gat | gac | ggc | aga | tac | aag | ggg | 575 |
| Gln | Tyr | Gln | Val | Val | Glu | Ile | Glu | Leu | Asp | Asp | Gly | Arg | Tyr | Lys | Gly | |

```
                  Gln Tyr Gln Val Val Glu Ile Glu Leu Asp Asp Gly Arg Tyr Lys Gly
                          180                 185                 190 atg ccc ttt gtt ctc cgg cgt ggt gaa aca tgg ata aag aac aac gac       623
Met Pro Phe Val Leu Arg Arg Gly Glu Thr Trp Ile Lys Asn Asn Asp
        195                 200                 205 tct gac ttc tat ttg gat ttc aac acc aaa gtt acc aag aaa tca aag       671
Ser Asp Phe Tyr Leu Asp Phe Asn Thr Lys Val Thr Lys Lys Ser Lys
    210                 215                 220 gat acg ggt gat gcc ggt aaa ggc acc gca aag gat ttc ctg gaa aga       719
Asp Thr Gly Asp Ala Gly Lys Gly Thr Ala Lys Asp Phe Leu Glu Arg
        225                 230                 235 ata gca gat ctg gag gaa gat gcc cag cga tct ttt atg cac aga ttt       767
Ile Ala Asp Leu Glu Glu Asp Ala Gln Arg Ser Phe Met His Arg Phe
240                 245                 250                 255 aat att gcg gcg gat cta gtt gac caa gcc aga gat gct gga cta ttg       815
Asn Ile Ala Ala Asp Leu Val Asp Gln Ala Arg Asp Ala Gly Leu Leu
                260                 265                 270 ggt atc gtt gga ctt ttt gtt tgg att aga ttc atg tct acc agg caa       863
Gly Ile Val Gly Leu Phe Val Trp Ile Arg Phe Met Ser Thr Arg Gln
            275                 280                 285 cta ata tgg aac aag aac tac aat gtg aaa cca cgt gag ata agc caa       911
Leu Ile Trp Asn Lys Asn Tyr Asn Val Lys Pro Arg Glu Ile Ser Gln
        290                 295                 300 gca caa gac agg ttt aca gat gac ctt gag aat atg tac aaa agt tac       959
Ala Gln Asp Arg Phe Thr Asp Asp Leu Glu Asn Met Tyr Lys Ser Tyr
    305                 310                 315 cca cag tac aga gag atc tta aga atg tta ttg tct gct gtt ggt cgt      1007
Pro Gln Tyr Arg Glu Ile Leu Arg Met Leu Leu Ser Ala Val Gly Arg
320                 325                 330                 335 gga ggt gaa ggt gat gtt ggt cag cgt atc cgt gat gag ata tta gta      1055
Gly Gly Glu Gly Asp Val Gly Gln Arg Ile Arg Asp Glu Ile Leu Val
                340                 345                 350 atc cag aga aat aat gac tgc aaa ggt gga att atg gaa gaa tgg cac      1103
Ile Gln Arg Asn Asn Asp Cys Lys Gly Gly Ile Met Glu Glu Trp His
            355                 360                 365 cag aaa ctg cac aac aat aca agc cca gat gat gta gtc ata tgc cag      1151
Gln Lys Leu His Asn Asn Thr Ser Pro Asp Asp Val Val Ile Cys Gln
        370                 375                 380 gcg ata att gat tat atc aag agc gat ttc gat atc aac gtt tac tgg      1199
Ala Ile Ile Asp Tyr Ile Lys Ser Asp Phe Asp Ile Asn Val Tyr Trp
    385                 390                 395 gac acc ttg aac aaa aat ggc ata acc aaa gaa cga ctg ttg agc tat      1247
Asp Thr Leu Asn Lys Asn Gly Ile Thr Lys Glu Arg Leu Leu Ser Tyr
400                 405                 410                 415 gat cgt gca att cat tca gaa cca aaa ttc agg agt gac cag aaa gag      1295
Asp Arg Ala Ile His Ser Glu Pro Lys Phe Arg Ser Asp Gln Lys Glu
                420                 425                 430 ggg tta ctc cgt gat ttg ggc aac tat atg aga agc ctg aag gct gtg      1343
Gly Leu Leu Arg Asp Leu Gly Asn Tyr Met Arg Ser Leu Lys Ala Val
            435                 440                 445 cac tct ggt gct gat ctt gag tct gct att gcg aca tgt atg gga tac      1391
His Ser Gly Ala Asp Leu Glu Ser Ala Ile Ala Thr Cys Met Gly Tyr
        450                 455                 460 aaa tca gag ggt gaa ggt ttc atg gtt ggt gtt caa atc aac ccg gtg      1439
Lys Ser Glu Gly Glu Gly Phe Met Val Gly Val Gln Ile Asn Pro Val
    465                 470                 475 aat ggt tta tca tct ggt ttt cct gat ttg ctt caa ttt gtg ctt gac      1487
Asn Gly Leu Ser Ser Gly Phe Pro Asp Leu Leu Gln Phe Val Leu Asp
480                 485                 490                 495
```

```
cat gtt gag gat aaa tca gca gag cca ctt ctt gag ggg tta ttg gag      1535
His Val Glu Asp Lys Ser Ala Glu Pro Leu Leu Glu Gly Leu Leu Glu
            500             505             510 gct cgt gtt gaa cta cgc cct ttg ctc act ggc tca tct gaa cgc ttg      1583
Ala Arg Val Glu Leu Arg Pro Leu Leu Thr Gly Ser Ser Glu Arg Leu
        515             520             525 aag gat ctt atc ttt ttg gac att gct ctt gat tct act ttc agg aca      1631
Lys Asp Leu Ile Phe Leu Asp Ile Ala Leu Asp Ser Thr Phe Arg Thr
    530             535             540 gca gtt gaa agg tcg tat gag gag ctg aat gat gca gca ccg gag aaa      1679
Ala Val Glu Arg Ser Tyr Glu Glu Leu Asn Asp Ala Ala Pro Glu Lys
545             550             555 att atg tac ttc atc agt ctt gtt ctt gaa aat ctt gcc ttg tcc act      1727
Ile Met Tyr Phe Ile Ser Leu Val Leu Glu Asn Leu Ala Leu Ser Thr
560             565             570             575 gac gac aac gaa gac atc tta tat tgc tta aag gga tgg aat cga gcc      1775
Asp Asp Asn Glu Asp Ile Leu Tyr Cys Leu Lys Gly Trp Asn Arg Ala
            580             585             590 atg gac atg gtt aag caa aag gat gac caa tgg gct ctc tac gct aaa      1823
Met Asp Met Val Lys Gln Lys Asp Asp Gln Trp Ala Leu Tyr Ala Lys
        595             600             605 gca ttt ctt gac aga acc aga ctt gcc ctt gcg agc aag ggc gaa caa      1871
Ala Phe Leu Asp Arg Thr Arg Leu Ala Leu Ala Ser Lys Gly Glu Gln
    610             615             620 tac tac aat atg atg cag ccc tcg gct gaa tat ctt ggc tca tta ctc      1919
Tyr Tyr Asn Met Met Gln Pro Ser Ala Glu Tyr Leu Gly Ser Leu Leu
625             630             635 aac gtt gag gaa tgg gct gtt gac atc ttc aca gaa gaa gta att cgt      1967
Asn Val Glu Glu Trp Ala Val Asp Ile Phe Thr Glu Glu Val Ile Arg
640             645             650             655 ggt gga tca gct gcc act tta tct gct ctt ctg aac cga ttt gac cct      2015
Gly Gly Ser Ala Ala Thr Leu Ser Ala Leu Leu Asn Arg Phe Asp Pro
            660             665             670 gtt ctc aga aat gtc gca cac ctt gga agt tgg cag gtt att agc cca      2063
Val Leu Arg Asn Val Ala His Leu Gly Ser Trp Gln Val Ile Ser Pro
        675             680             685 gtt gaa gta aca ggt tat att gta gtg gtt gat aag ttg ctt tct gtt      2111
Val Glu Val Thr Gly Tyr Ile Val Val Val Asp Lys Leu Leu Ser Val
    690             695             700 caa aac aaa act tat gat aaa cca aca atc ctt gtg gca aag agt gtc      2159
Gln Asn Lys Thr Tyr Asp Lys Pro Thr Ile Leu Val Ala Lys Ser Val
705             710             715 aag gga gag gaa gaa ata cca gat ggt gtt gtt ggc gtg ata aca cct      2207
Lys Gly Glu Glu Glu Ile Pro Asp Gly Val Val Gly Val Ile Thr Pro
720             725             730             735 gat atg cca gat gtt ctg tct cat gtg tca gtt cga gca agg aat tgc      2255
Asp Met Pro Asp Val Leu Ser His Val Ser Val Arg Ala Arg Asn Cys
            740             745             750 aag gtg ttg ttt gcg aca tgc ttt gac ccg aat acc ctg tct gaa ttt      2303
Lys Val Leu Phe Ala Thr Cys Phe Asp Pro Asn Thr Leu Ser Glu Phe
        755             760             765 caa gga cat gaa ggg aag gtg ttt tcc ttc aaa act act tct gca gat      2351
Gln Gly His Glu Gly Lys Val Phe Ser Phe Lys Thr Thr Ser Ala Asp
    770             775             780 gtc acc tac agg gag gta tcg gac agt gaa ctt atg cag tca agt tct      2399
Val Thr Tyr Arg Glu Val Ser Asp Ser Glu Leu Met Gln Ser Ser Ser
785             790             795 tca gat gca caa ggt ggt gaa gca ata cca tct tta tca tta gtc aag      2447
Ser Asp Ala Gln Gly Gly Glu Ala Ile Pro Ser Leu Ser Leu Val Lys
800             805             810             815
```

-continued

| | |
|---|---|
| aaa aag ttc ctt gga aaa tat gca ata tca gcg gaa gag ttc tct gat<br>Lys Lys Phe Leu Gly Lys Tyr Ala Ile Ser Ala Glu Glu Phe Ser Asp<br>               820                   825                 830 | 2495 |
| gaa atg gtt gga gca aag tcc cgc aac ata gca tac ctg aaa gga aaa<br>Glu Met Val Gly Ala Lys Ser Arg Asn Ile Ala Tyr Leu Lys Gly Lys<br>               835                   840                 845 | 2543 |
| gta cct tca tgg gtt ggt atc cca aca tca gtt gcg ata cca ttt ggg<br>Val Pro Ser Trp Val Gly Ile Pro Thr Ser Val Ala Ile Pro Phe Gly<br>850                   855                   860 | 2591 |
| acc ttt gag aag ata ttg tct gat gag acc aat aag gaa gta gca caa<br>Thr Phe Glu Lys Ile Leu Ser Asp Glu Thr Asn Lys Glu Val Ala Gln<br>    865                   870                 875 | 2639 |
| aac ata cag atg ctg aag ggc aga ctt gct caa gaa gat ttt agt gct<br>Asn Ile Gln Met Leu Lys Gly Arg Leu Ala Gln Glu Asp Phe Ser Ala<br>880                   885                   890                 895 | 2687 |
| cta gga gaa atc cgg aaa act gtt ctt aat cta act gct cca act caa<br>Leu Gly Glu Ile Arg Lys Thr Val Leu Asn Leu Thr Ala Pro Thr Gln<br>               900                   905                 910 | 2735 |
| ccg gtt aag gag ctg aag gag aag atg cta agc tcc gga atg ccc tgg<br>Pro Val Lys Glu Leu Lys Glu Lys Met Leu Ser Ser Gly Met Pro Trp<br>             915                   920                 925 | 2783 |
| cct gga gat gaa agt gac cac cgt tgg gag caa gca tgg atg gca att<br>Pro Gly Asp Glu Ser Asp His Arg Trp Glu Gln Ala Trp Met Ala Ile<br>930                   935                   940 | 2831 |
| aaa aag gtt tgg gca tca aaa tgg aat gaa aga gca tac ttt agt aca<br>Lys Lys Val Trp Ala Ser Lys Trp Asn Glu Arg Ala Tyr Phe Ser Thr<br>    945                   950                 955 | 2879 |
| cgc aag gtg aag ctc gat cat gag tac ctt tcc atg gct gtt ctt gta<br>Arg Lys Val Lys Leu Asp His Glu Tyr Leu Ser Met Ala Val Leu Val<br>960                   965                   970                 975 | 2927 |
| caa gaa att gtc aac gca gac tat gcc ttt gtc att cat act acg aac<br>Gln Glu Ile Val Asn Ala Asp Tyr Ala Phe Val Ile His Thr Thr Asn<br>             980                   985                 990 | 2975 |
| ccg tca tct gga gat tct tct gag ata tat gct gaa gtg gtg aaa gga<br>Pro Ser Ser Gly Asp Ser Ser Glu Ile Tyr Ala Glu Val Val Lys Gly<br>          995                 1000              1005 | 3023 |
| ctt gga gag aca ctt gtg gga gct tat cct ggc cgt gcc atg agc<br>Leu Gly Glu Thr Leu Val Gly Ala Tyr Pro Gly Arg Ala Met Ser<br>        1010                1015               1020 | 3068 |
| ttc gtg tgt aag aaa gat gac ctt gac tct ccc aag gta ctg ggt<br>Phe Val Cys Lys Lys Asp Asp Leu Asp Ser Pro Lys Val Leu Gly<br>1025                1030                1035 | 3113 |
| tac cct agc aag cca att ggt ctc ttc ata aag cgg tca atc atc<br>Tyr Pro Ser Lys Pro Ile Gly Leu Phe Ile Lys Arg Ser Ile Ile<br>        1040                1045                1050 | 3158 |
| ttc cgc tca gac tct aat ggt gag gat ctg gaa ggt tac gct gga<br>Phe Arg Ser Asp Ser Asn Gly Glu Asp Leu Glu Gly Tyr Ala Gly<br>1055                1060                1065 | 3203 |
| gca ggg ctg tat gat agt gtc cct atg gat gtg gaa gat gaa gtt<br>Ala Gly Leu Tyr Asp Ser Val Pro Met Asp Val Glu Asp Glu Val<br>        1070                1075                1080 | 3248 |
| gta ctc gac tac acg acc gac cct ctc atc act gac tct gga ttc<br>Val Leu Asp Tyr Thr Thr Asp Pro Leu Ile Thr Asp Ser Gly Phe<br>1085                1090                1095 | 3293 |
| cgg aac tca atc ctc tca agc att gca cgg gct ggc cac gcc atc<br>Arg Asn Ser Ile Leu Ser Ser Ile Ala Arg Ala Gly His Ala Ile<br>        1100                1105                1110 | 3338 |
| gag gag ctc tat ggg tca cca cag gat gtt gag gga gta gtg aag<br>Glu Glu Leu Tyr Gly Ser Pro Gln Asp Val Glu Gly Val Val Lys | 3383 |

-continued

```
                  1115                1120                1125
gat  ggg  aag  atc  tac  gta  gtc  cag  aca  tac  cac  ag                    3418
Asp  Gly  Lys  Ile  Tyr  Val  Val  Gln  Thr  Tyr  His
              1130                1135
```

<210> SEQ ID NO 8
<211> LENGTH: 1138
<212> TYPE: PRT
<213> ORGANISM: Triticum aestivum

<400> SEQUENCE: 8

```
Gly Arg Arg Lys Glu Leu Gln Ala Glu Leu Asp Asn Gly Ala Ser Val
1               5                   10                  15

Asp Gln Leu Arg Lys Lys Ile Val Lys Gly Asn Leu Glu Lys Lys Val
                20                  25                  30

Ser Lys Gln Leu Glu Lys Lys Tyr Phe Ser Val Glu Arg Ile Gln
            35                  40                  45

Arg Arg Asn Arg Asp Ile Thr Gln Leu Leu Asn Lys His Lys Pro Val
50                  55                  60

Val Thr Glu Gln Gln Val Lys Ala Ala Pro Lys Gln Pro Thr Val Leu
65                  70                  75                  80

Asp Leu Phe Thr Lys Ser Leu Gln Glu Gly Asp Asn Cys Asp Val Leu
                85                  90                  95

Ser Arg Lys Leu Phe Lys Ile Gly Asp Glu Ile Leu Ala Ile Ala
            100                 105                 110

Thr Asn Ala Leu Gly Lys Thr Arg Val His Leu Ala Thr Asn Arg Met
        115                 120                 125

Glu Pro Leu Ile Leu His Trp Ala Leu Ala Lys Asn Pro Gly Glu Trp
130                 135                 140

Glu Ala Pro Pro Ser Ser Ile Val Pro Ser Gly Ser Thr Val Leu Asp
145                 150                 155                 160

Lys Ala Cys Glu Thr Ser Phe Gly Glu Ser Glu Leu Asp Gly Leu Gln
                165                 170                 175

Tyr Gln Val Val Glu Ile Glu Leu Asp Asp Gly Arg Tyr Lys Gly Met
            180                 185                 190

Pro Phe Val Leu Arg Arg Gly Glu Thr Trp Ile Lys Asn Asn Asp Ser
        195                 200                 205

Asp Phe Tyr Leu Asp Phe Asn Thr Lys Val Thr Lys Lys Ser Lys Asp
    210                 215                 220

Thr Gly Asp Ala Gly Lys Gly Thr Ala Lys Asp Phe Leu Glu Arg Ile
225                 230                 235                 240

Ala Asp Leu Glu Glu Asp Ala Gln Arg Ser Phe Met His Arg Phe Asn
                245                 250                 255

Ile Ala Ala Asp Leu Val Asp Gln Ala Arg Asp Ala Gly Leu Leu Gly
            260                 265                 270

Ile Val Gly Leu Phe Val Trp Ile Arg Phe Met Ser Thr Arg Gln Leu
        275                 280                 285

Ile Trp Asn Lys Asn Tyr Asn Val Lys Pro Arg Glu Ile Ser Gln Ala
    290                 295                 300

Gln Asp Arg Phe Thr Asp Asp Leu Glu Asn Met Tyr Lys Ser Tyr Pro
305                 310                 315                 320

Gln Tyr Arg Glu Ile Leu Arg Met Leu Leu Ser Ala Val Gly Arg Gly
                325                 330                 335

Gly Glu Gly Asp Val Gly Gln Arg Ile Arg Asp Glu Ile Leu Val Ile
            340                 345                 350
```

```
Gln Arg Asn Asn Asp Cys Lys Gly Gly Ile Met Glu Glu Trp His Gln
            355                 360                 365
Lys Leu His Asn Asn Thr Ser Pro Asp Val Val Ile Cys Gln Ala
        370                 375                 380
Ile Ile Asp Tyr Ile Lys Ser Asp Phe Asp Ile Asn Val Tyr Trp Asp
385                 390                 395                 400
Thr Leu Asn Lys Asn Gly Ile Thr Lys Glu Arg Leu Leu Ser Tyr Asp
                405                 410                 415
Arg Ala Ile His Ser Glu Pro Lys Phe Arg Ser Asp Gln Lys Glu Gly
            420                 425                 430
Leu Leu Arg Asp Leu Gly Asn Tyr Met Arg Ser Leu Lys Ala Val His
        435                 440                 445
Ser Gly Ala Asp Leu Glu Ser Ala Ile Ala Thr Cys Met Gly Tyr Lys
    450                 455                 460
Ser Glu Gly Glu Gly Phe Met Val Gly Val Gln Ile Asn Pro Val Asn
465                 470                 475                 480
Gly Leu Ser Ser Gly Phe Pro Asp Leu Leu Gln Phe Val Leu Asp His
                485                 490                 495
Val Glu Asp Lys Ser Ala Glu Pro Leu Leu Glu Gly Leu Leu Glu Ala
            500                 505                 510
Arg Val Glu Leu Arg Pro Leu Leu Thr Gly Ser Ser Glu Arg Leu Lys
        515                 520                 525
Asp Leu Ile Phe Leu Asp Ile Ala Leu Asp Ser Thr Phe Arg Thr Ala
    530                 535                 540
Val Glu Arg Ser Tyr Glu Glu Leu Asn Asp Ala Ala Pro Glu Lys Ile
545                 550                 555                 560
Met Tyr Phe Ile Ser Leu Val Leu Glu Asn Leu Ala Leu Ser Thr Asp
                565                 570                 575
Asp Asn Glu Asp Ile Leu Tyr Cys Leu Lys Gly Trp Asn Arg Ala Met
            580                 585                 590
Asp Met Val Lys Gln Lys Asp Asp Gln Trp Ala Leu Tyr Ala Lys Ala
        595                 600                 605
Phe Leu Asp Arg Thr Arg Leu Ala Leu Ala Ser Lys Gly Glu Gln Tyr
    610                 615                 620
Tyr Asn Met Met Gln Pro Ser Ala Glu Tyr Leu Gly Ser Leu Leu Asn
625                 630                 635                 640
Val Glu Glu Trp Ala Val Asp Ile Phe Thr Glu Glu Val Ile Arg Gly
                645                 650                 655
Gly Ser Ala Ala Thr Leu Ser Ala Leu Leu Asn Arg Phe Asp Pro Val
            660                 665                 670
Leu Arg Asn Val Ala His Leu Gly Ser Trp Gln Val Ile Ser Pro Val
        675                 680                 685
Glu Val Thr Gly Tyr Ile Val Val Asp Lys Leu Leu Ser Val Gln
    690                 695                 700
Asn Lys Thr Tyr Asp Lys Pro Thr Ile Leu Val Ala Lys Ser Val Lys
705                 710                 715                 720
Gly Glu Glu Glu Ile Pro Asp Gly Val Val Gly Val Ile Thr Pro Asp
                725                 730                 735
Met Pro Asp Val Leu Ser His Val Ser Val Arg Ala Arg Asn Cys Lys
            740                 745                 750
Val Leu Phe Ala Thr Cys Phe Asp Pro Asn Thr Leu Ser Glu Phe Gln
        755                 760                 765
```

-continued

```
Gly His Glu Gly Lys Val Phe Ser Phe Lys Thr Thr Ser Ala Asp Val
    770                 775                 780

Thr Tyr Arg Glu Val Ser Asp Ser Glu Leu Met Gln Ser Ser Ser Ser
785                 790                 795                 800

Asp Ala Gln Gly Gly Glu Ala Ile Pro Ser Leu Ser Leu Val Lys Lys
                805                 810                 815

Lys Phe Leu Gly Lys Tyr Ala Ile Ser Ala Glu Glu Phe Ser Asp Glu
                820                 825                 830

Met Val Gly Ala Lys Ser Arg Asn Ile Ala Tyr Leu Lys Gly Lys Val
                835                 840                 845

Pro Ser Trp Val Gly Ile Pro Thr Ser Val Ala Ile Pro Phe Gly Thr
                850                 855                 860

Phe Glu Lys Ile Leu Ser Asp Glu Thr Asn Lys Glu Val Ala Gln Asn
865                 870                 875                 880

Ile Gln Met Leu Lys Gly Arg Leu Ala Gln Glu Asp Phe Ser Ala Leu
                885                 890                 895

Gly Glu Ile Arg Lys Thr Val Leu Asn Leu Thr Ala Pro Thr Gln Pro
                900                 905                 910

Val Lys Glu Leu Lys Glu Lys Met Leu Ser Ser Gly Met Pro Trp Pro
                915                 920                 925

Gly Asp Glu Ser Asp His Arg Trp Glu Gln Ala Trp Met Ala Ile Lys
                930                 935                 940

Lys Val Trp Ala Ser Lys Trp Asn Glu Arg Ala Tyr Phe Ser Thr Arg
945                 950                 955                 960

Lys Val Lys Leu Asp His Glu Tyr Leu Ser Met Ala Val Leu Val Gln
                965                 970                 975

Glu Ile Val Asn Ala Asp Tyr Ala Phe Val Ile His Thr Thr Asn Pro
                980                 985                 990

Ser Ser Gly Asp Ser Ser Glu Ile Tyr Ala Glu Val Val Lys Gly Leu
                995                 1000                1005

Gly Glu Thr Leu Val Gly Ala Tyr Pro Gly Arg Ala Met Ser Phe
    1010                1015                1020

Val Cys Lys Lys Asp Asp Leu Asp Ser Pro Lys Val Leu Gly Tyr
    1025                1030                1035

Pro Ser Lys Pro Ile Gly Leu Phe Ile Lys Arg Ser Ile Ile Phe
    1040                1045                1050

Arg Ser Asp Ser Asn Gly Glu Asp Leu Glu Gly Tyr Ala Gly Ala
    1055                1060                1065

Gly Leu Tyr Asp Ser Val Pro Met Asp Val Glu Asp Glu Val Val
    1070                1075                1080

Leu Asp Tyr Thr Thr Asp Pro Leu Ile Thr Asp Ser Gly Phe Arg
    1085                1090                1095

Asn Ser Ile Leu Ser Ser Ile Ala Arg Ala Gly His Ala Ile Glu
    1100                1105                1110

Glu Leu Tyr Gly Ser Pro Gln Asp Val Glu Gly Val Val Lys Asp
    1115                1120                1125

Gly Lys Ile Tyr Val Val Gln Thr Tyr His
    1130                1135

<210> SEQ ID NO 9
<211> LENGTH: 3678
<212> TYPE: DNA
<213> ORGANISM: Triticum aestivum
<220> FEATURE:
<221> NAME/KEY: CDS
```

-continued

<222> LOCATION: (3)..(3458)

<400> SEQUENCE: 9

```
ga gga aga agg aag gaa ctg cag gct gag ttg gat aat gga gcc tca        47
   Gly Arg Arg Lys Glu Leu Gln Ala Glu Leu Asp Asn Gly Ala Ser
   1               5                  10                  15 gtt gat caa tta agg aag aaa att gtg aaa gga aac ctt gaa aag aaa        95
Val Asp Gln Leu Arg Lys Lys Ile Val Lys Gly Asn Leu Glu Lys Lys
            20                  25                  30 gtt tcc aag caa ctg gag aag aag aag tac ttc tca gta gaa agg att       143
Val Ser Lys Gln Leu Glu Lys Lys Lys Tyr Phe Ser Val Glu Arg Ile
        35                  40                  45 cag cgc aga aac aga gat atc acg caa ctt ctt aat aaa cat aag cct       191
Gln Arg Arg Asn Arg Asp Ile Thr Gln Leu Leu Asn Lys His Lys Pro
    50                  55                  60 gtg gtt aca gaa cag caa gta aaa gct gca ccc aaa cag cca act gtt       239
Val Val Thr Glu Gln Gln Val Lys Ala Ala Pro Lys Gln Pro Thr Val
65                  70                  75 ttg gat ctc ttc aca aag tcc ttg caa gag ggg gat aac tgt gac gtc       287
Leu Asp Leu Phe Thr Lys Ser Leu Gln Glu Gly Asp Asn Cys Asp Val
80                  85                  90                  95 cta agc agg aag ctt ttc aag atc ggt gat gag gag ata ctg gca att       335
Leu Ser Arg Lys Leu Phe Lys Ile Gly Asp Glu Glu Ile Leu Ala Ile
                100                 105                 110 gcc aca aat gct cta ggt aaa acc aga gtt cac ttg gca aca aac cgt       383
Ala Thr Asn Ala Leu Gly Lys Thr Arg Val His Leu Ala Thr Asn Arg
            115                 120                 125 atg gag cca ctt att ctt cac tgg gca ctg gca aaa aat ccc gga gaa       431
Met Glu Pro Leu Ile Leu His Trp Ala Leu Ala Lys Asn Pro Gly Glu
        130                 135                 140 tgg gag gca cct cct tct agc ata gtg cct tct ggc tca aca gtt ctc       479
Trp Glu Ala Pro Pro Ser Ser Ile Val Pro Ser Gly Ser Thr Val Leu
    145                 150                 155 gac aag gca tgt gaa act tca ttc ggt gag tct gaa ttg gat ggt ttg       527
Asp Lys Ala Cys Glu Thr Ser Phe Gly Glu Ser Glu Leu Asp Gly Leu
160                 165                 170                 175 caa tac cag gtt gtt gag ata gag ctt gat gac ggc aga tac aag ggg       575
Gln Tyr Gln Val Val Glu Ile Glu Leu Asp Asp Gly Arg Tyr Lys Gly
                180                 185                 190 atg ccc ttt gtt ctc cgg cgt ggt gaa aca tgg ata aag aac aac gac       623
Met Pro Phe Val Leu Arg Arg Gly Glu Thr Trp Ile Lys Asn Asn Asp
            195                 200                 205 tct gac ttc tat ttg gat ttc aac acc aaa gtt acc aag aaa tca aag       671
Ser Asp Phe Tyr Leu Asp Phe Asn Thr Lys Val Thr Lys Lys Ser Lys
        210                 215                 220 gat acg ggt gat gcc ggt aaa ggc acc gca aag gat ttc ctg gaa aga       719
Asp Thr Gly Asp Ala Gly Lys Gly Thr Ala Lys Asp Phe Leu Glu Arg
    225                 230                 235 ata gca gat ctg gag gaa gat gcc cag cga tct ttt atg cac aga ttt       767
Ile Ala Asp Leu Glu Glu Asp Ala Gln Arg Ser Phe Met His Arg Phe
240                 245                 250                 255 aat att gcg gcg gat cta gtt gac caa gcc aga gat gct gga cta ttg       815
Asn Ile Ala Ala Asp Leu Val Asp Gln Ala Arg Asp Ala Gly Leu Leu
                260                 265                 270 ggt atc gtt gga ctt ttt gtt tgg att aga ttc atg tct acc agg caa       863
Gly Ile Val Gly Leu Phe Val Trp Ile Arg Phe Met Ser Thr Arg Gln
            275                 280                 285 cta ata tgg aac aag aac tac aat gtg aaa cca cgt gag ata agc caa       911
Leu Ile Trp Asn Lys Asn Tyr Asn Val Lys Pro Arg Glu Ile Ser Gln
        290                 295                 300
```

```
                                                              -continued gca caa gac agg ttt aca gat gac ctt gag aat atg tac aaa agt tac      959
Ala Gln Asp Arg Phe Thr Asp Asp Leu Glu Asn Met Tyr Lys Ser Tyr
    305                 310                 315 cca cag tac aga gag atc tta aga atg tta ttg tct gct gtt ggt cgt     1007
Pro Gln Tyr Arg Glu Ile Leu Arg Met Leu Leu Ser Ala Val Gly Arg
320                 325                 330                 335 gga ggt gaa ggt gat gtt ggt cag cgt atc cgt gat gag ata tta gta     1055
Gly Gly Glu Gly Asp Val Gly Gln Arg Ile Arg Asp Glu Ile Leu Val
                340                 345                 350 atc cag aga aat aat gac tgc aaa ggt gga att atg gaa gaa tgg cac     1103
Ile Gln Arg Asn Asn Asp Cys Lys Gly Gly Ile Met Glu Glu Trp His
        355                 360                 365 cag aaa ctg cac aac aat aca agc cca gat gat gta gtc ata tgc cag     1151
Gln Lys Leu His Asn Asn Thr Ser Pro Asp Asp Val Val Ile Cys Gln
    370                 375                 380 gcg ata att gat tat atc aag agc gat ttc gat atc aac gtt tac tgg     1199
Ala Ile Ile Asp Tyr Ile Lys Ser Asp Phe Asp Ile Asn Val Tyr Trp
385                 390                 395 gac acc ttg aac aaa aat ggc ata acc aaa gaa cga ctg ttg agc tat     1247
Asp Thr Leu Asn Lys Asn Gly Ile Thr Lys Glu Arg Leu Leu Ser Tyr
400                 405                 410                 415 gat cgt gca att cat tca gaa cca aaa ttc agg agt gac cag aaa gag     1295
Asp Arg Ala Ile His Ser Glu Pro Lys Phe Arg Ser Asp Gln Lys Glu
                420                 425                 430 ggg tta ctc cgt gat ttg ggc aac tat atg aga agc ctg aag gct gtg     1343
Gly Leu Leu Arg Asp Leu Gly Asn Tyr Met Arg Ser Leu Lys Ala Val
        435                 440                 445 cac tct ggt gct gat ctt gag tct gct att gcg aca tgt atg gga tac     1391
His Ser Gly Ala Asp Leu Glu Ser Ala Ile Ala Thr Cys Met Gly Tyr
    450                 455                 460 aaa tca gag ggt gaa ggt ttc atg gtt ggt gtt caa atc aac ccg gtg     1439
Lys Ser Glu Gly Glu Gly Phe Met Val Gly Val Gln Ile Asn Pro Val
465                 470                 475 aat ggt tta tca tct ggt ttt cct gat ttg ctt caa ttt gtg ctt gac     1487
Asn Gly Leu Ser Ser Gly Phe Pro Asp Leu Leu Gln Phe Val Leu Asp
480                 485                 490                 495 cat gtt gag gat aaa tca gca gag cca ctt ctt gag ggg tta ttg gag     1535
His Val Glu Asp Lys Ser Ala Glu Pro Leu Leu Glu Gly Leu Leu Glu
                500                 505                 510 gct cgt gtt gaa cta cgc cct ttg ctc act ggc tca tct gaa cgc ttg     1583
Ala Arg Val Glu Leu Arg Pro Leu Leu Thr Gly Ser Ser Glu Arg Leu
        515                 520                 525 aag gat ctt atc ttt ttg gac att gct ctt gat tct act ttc agg aca     1631
Lys Asp Leu Ile Phe Leu Asp Ile Ala Leu Asp Ser Thr Phe Arg Thr
    530                 535                 540 gca gtt gaa agg tcg tat gag gag ctg aat gat gca gca ccg gag aaa     1679
Ala Val Glu Arg Ser Tyr Glu Glu Leu Asn Asp Ala Ala Pro Glu Lys
545                 550                 555 att atg tac ttc atc agt ctt gtt ctt gaa aat ctt gcc ttg tcc act     1727
Ile Met Tyr Phe Ile Ser Leu Val Leu Glu Asn Leu Ala Leu Ser Thr
560                 565                 570                 575 gac gac aac gaa gac atc tta tat tgc tta aag gga tgg aat cga gcc     1775
Asp Asp Asn Glu Asp Ile Leu Tyr Cys Leu Lys Gly Trp Asn Arg Ala
                580                 585                 590 atg gac atg gtt aag caa aag gat gac caa tgg gct ctc tac gct aaa     1823
Met Asp Met Val Lys Gln Lys Asp Asp Gln Trp Ala Leu Tyr Ala Lys
        595                 600                 605 gca ttt ctt gac aga acc aga ctt gcc ctt gcg agc aag ggc gaa caa     1871
Ala Phe Leu Asp Arg Thr Arg Leu Ala Leu Ala Ser Lys Gly Glu Gln
```

```
                                                              -continued 610                    615                     620
tac  tac  aat  atg  atg  cag  ccc  tcg  gct  gaa  tat  ctt  ggc  tca  tta  ctc          1919
Tyr  Tyr  Asn  Met  Met  Gln  Pro  Ser  Ala  Glu  Tyr  Leu  Gly  Ser  Leu  Leu
          625                    630                     635 aac  gtt  gag  gaa  tgg  gct  gtt  gac  atc  ttc  aca  gaa  gaa  gta  att  cgt          1967
Asn  Val  Glu  Glu  Trp  Ala  Val  Asp  Ile  Phe  Thr  Glu  Glu  Val  Ile  Arg
640                    645                    650                     655 ggt  gga  tca  gct  gcc  act  tta  tct  gct  ctt  ctg  aac  cga  ttt  gac  cct          2015
Gly  Gly  Ser  Ala  Ala  Thr  Leu  Ser  Ala  Leu  Leu  Asn  Arg  Phe  Asp  Pro
                    660                    665                     670 gtt  ctc  aga  aat  gtc  gca  cac  ctt  gga  agt  tgg  cag  gtt  att  agc  cca          2063
Val  Leu  Arg  Asn  Val  Ala  His  Leu  Gly  Ser  Trp  Gln  Val  Ile  Ser  Pro
               675                    680                     685 gtt  gaa  gta  aca  ggt  tat  att  gta  gtg  gtt  gat  aag  ttg  ctt  tct  gtt          2111
Val  Glu  Val  Thr  Gly  Tyr  Ile  Val  Val  Val  Asp  Lys  Leu  Leu  Ser  Val
          690                    695                    700 caa  aac  aaa  act  tat  gat  aaa  cca  aca  atc  ctt  gtg  gca  aag  agt  gtc          2159
Gln  Asn  Lys  Thr  Tyr  Asp  Lys  Pro  Thr  Ile  Leu  Val  Ala  Lys  Ser  Val
     705                    710                    715 aag  gga  gag  gaa  gaa  ata  cca  gat  ggt  gtt  gtt  ggc  gtg  ata  aca  cct          2207
Lys  Gly  Glu  Glu  Glu  Ile  Pro  Asp  Gly  Val  Val  Gly  Val  Ile  Thr  Pro
720                    725                    730                     735 gat  atg  cca  gat  gtt  ctg  tct  cat  gtg  tca  gtt  cga  gca  agg  aat  tgc          2255
Asp  Met  Pro  Asp  Val  Leu  Ser  His  Val  Ser  Val  Arg  Ala  Arg  Asn  Cys
                    740                    745                     750 aag  gtg  ttg  ttt  gcg  aca  tgc  ttt  gac  ccg  aat  acc  ctg  tct  gaa  ttt          2303
Lys  Val  Leu  Phe  Ala  Thr  Cys  Phe  Asp  Pro  Asn  Thr  Leu  Ser  Glu  Phe
               755                    760                    765 caa  gga  cat  gaa  ggg  aag  gtg  ttt  tcc  ttc  aaa  act  act  tct  gca  gat          2351
Gln  Gly  His  Glu  Gly  Lys  Val  Phe  Ser  Phe  Lys  Thr  Thr  Ser  Ala  Asp
          770                    775                    780 gtc  acc  tac  agg  gag  gta  tcg  gac  agt  gaa  ctt  atg  cag  tca  agt  tct          2399
Val  Thr  Tyr  Arg  Glu  Val  Ser  Asp  Ser  Glu  Leu  Met  Gln  Ser  Ser  Ser
     785                    790                    795 tca  gat  gca  caa  ggt  ggt  gaa  gca  ata  cca  tct  tta  tca  tta  gtc  aag          2447
Ser  Asp  Ala  Gln  Gly  Gly  Glu  Ala  Ile  Pro  Ser  Leu  Ser  Leu  Val  Lys
800                    805                    810                     815 aaa  aag  ttc  ctt  gga  aaa  tat  gca  ata  tca  gcg  gaa  gag  ttc  tct  gat          2495
Lys  Lys  Phe  Leu  Gly  Lys  Tyr  Ala  Ile  Ser  Ala  Glu  Glu  Phe  Ser  Asp
                    820                    825                     830 gaa  atg  gtt  gga  gca  aag  tcc  cgc  aac  ata  gca  tac  ctg  aaa  gga  aaa          2543
Glu  Met  Val  Gly  Ala  Lys  Ser  Arg  Asn  Ile  Ala  Tyr  Leu  Lys  Gly  Lys
               835                    840                    845 gta  cct  tca  tgg  gtt  ggt  atc  cca  aca  tca  gtt  gcg  ata  cca  ttt  ggg          2591
Val  Pro  Ser  Trp  Val  Gly  Ile  Pro  Thr  Ser  Val  Ala  Ile  Pro  Phe  Gly
          850                    855                    860 acc  ttt  gag  aag  ata  ttg  tct  gat  gag  acc  aat  aag  gaa  gta  gca  caa          2639
Thr  Phe  Glu  Lys  Ile  Leu  Ser  Asp  Glu  Thr  Asn  Lys  Glu  Val  Ala  Gln
     865                    870                    875 aac  ata  cag  atg  ctg  aag  ggc  aga  ctt  gct  caa  gaa  gat  ttt  agt  gct          2687
Asn  Ile  Gln  Met  Leu  Lys  Gly  Arg  Leu  Ala  Gln  Glu  Asp  Phe  Ser  Ala
880                    885                    890                     895 cta  gga  gaa  atc  cgg  aaa  act  gtt  ctt  aat  cta  act  gct  cca  act  caa          2735
Leu  Gly  Glu  Ile  Arg  Lys  Thr  Val  Leu  Asn  Leu  Thr  Ala  Pro  Thr  Gln
                    900                    905                     910 ccg  gtt  aag  gag  ctg  aag  gag  aag  atg  cta  agc  tcc  gga  atg  ccc  tgg          2783
Pro  Val  Lys  Glu  Leu  Lys  Glu  Lys  Met  Leu  Ser  Ser  Gly  Met  Pro  Trp
               915                    920                    925 cct  gga  gat  gaa  agt  gac  cac  cgt  tgg  gag  caa  gca  tgg  atg  gca  att          2831
```

-continued

```
              Pro Gly Asp Glu Ser Asp His Arg Trp Glu Gln Ala Trp Met Ala Ile
                      930                 935                 940 aaa aag gtt tgg gca tca aaa tgg aat gaa aga gca tac ttt agt aca         2879
Lys Lys Val Trp Ala Ser Lys Trp Asn Glu Arg Ala Tyr Phe Ser Thr
        945                 950                 955 cgc aag gtg aag ctc gat cat gag tac ctt tcc atg gct gtt ctt gta         2927
Arg Lys Val Lys Leu Asp His Glu Tyr Leu Ser Met Ala Val Leu Val
960                 965                 970                 975 caa gaa att gtc aac gca gac tat gcc ttt gtc att cat act acg aac         2975
Gln Glu Ile Val Asn Ala Asp Tyr Ala Phe Val Ile His Thr Thr Asn
                980                 985                 990 ccg tca tct gga gat tct tct gag ata tat gct gaa gtg gtg aaa gga         3023
Pro Ser Ser Gly Asp Ser Ser Glu Ile Tyr Ala Glu Val Val Lys Gly
                995                 1000                1005 ctt gga gag aca ctt gtg gga gct tat cct ggc cgt gcc atg agc             3068
Leu Gly Glu Thr Leu Val Gly Ala Tyr Pro Gly Arg Ala Met Ser
            1010                1015                1020 ttc gtg tgt aag aaa gat gac ctt gac tct ccc aag gta ctg ggt             3113
Phe Val Cys Lys Lys Asp Asp Leu Asp Ser Pro Lys Val Leu Gly
            1025                1030                1035 tac cct agc aag cca att ggt ctc ttc ata aag cgg tca atc atc             3158
Tyr Pro Ser Lys Pro Ile Gly Leu Phe Ile Lys Arg Ser Ile Ile
            1040                1045                1050 ttc cgc tca gac tct aat ggt gag gat ctg gaa ggt tac gct gga             3203
Phe Arg Ser Asp Ser Asn Gly Glu Asp Leu Glu Gly Tyr Ala Gly
            1055                1060                1065 gca ggg ctg tat gat agt gtc cct atg gat gtg gaa gat gaa gtt             3248
Ala Gly Leu Tyr Asp Ser Val Pro Met Asp Val Glu Asp Glu Val
            1070                1075                1080 gta ctc gac tac acg acc gac cct ctc atc act gac tct gga ttc             3293
Val Leu Asp Tyr Thr Thr Asp Pro Leu Ile Thr Asp Ser Gly Phe
            1085                1090                1095 cgg aac tca atc ctc tca agc att gca cgg gct ggc cac gcc atc             3338
Arg Asn Ser Ile Leu Ser Ser Ile Ala Arg Ala Gly His Ala Ile
            1100                1105                1110 gag gag ctc tat ggg tca cca cag gat gtt gag gga gta gtg aag             3383
Glu Glu Leu Tyr Gly Ser Pro Gln Asp Val Glu Gly Val Val Lys
            1115                1120                1125 gat ggg aag atc tac gta gtc cag aca tac cac aga tgt aat atg             3428
Asp Gly Lys Ile Tyr Val Val Gln Thr Tyr His Arg Cys Asn Met
            1130                1135                1140 tat gta tac gcg gct caa gtt gta gag tag taggatatat ggtccttgct           3478
Tyr Val Tyr Ala Ala Gln Val Val Glu
            1145                1150 ggcatgtata gttgtactca taggtgcaca acacatctac gttgttattt atttgcatat       3538
acgctcagaa taagctttga tcacatactg tatttcctag agtaccagaa agtgtatgta       3598
cgatcaggaa tatgacctta ttaaaaccat tgagggaaa tgttttgact tttgagcaat        3658
ctaaaaaaaa aaaaaaaaa                                                    3678

<210> SEQ ID NO 10
<211> LENGTH: 1151
<212> TYPE: PRT
<213> ORGANISM: Triticum aestivum

<400> SEQUENCE: 10

Gly Arg Arg Lys Glu Leu Gln Ala Glu Leu Asp Asn Gly Ala Ser Val
1               5                   10                  15

Asp Gln Leu Arg Lys Lys Ile Val Lys Gly Asn Leu Glu Lys Lys Val
```

```
                      20                  25                  30
Ser Lys Gln Leu Glu Lys Lys Tyr Phe Ser Val Glu Arg Ile Gln
         35                  40                  45

Arg Arg Asn Arg Asp Ile Thr Gln Leu Leu Asn Lys His Lys Pro Val
 50                  55                  60

Val Thr Glu Gln Gln Val Lys Ala Ala Pro Lys Gln Pro Thr Val Leu
 65                  70                  75                  80

Asp Leu Phe Thr Lys Ser Leu Gln Glu Gly Asp Asn Cys Asp Val Leu
             85                  90                  95

Ser Arg Lys Leu Phe Lys Ile Gly Asp Glu Ile Leu Ala Ile Ala
         100                 105                 110

Thr Asn Ala Leu Gly Lys Thr Arg Val His Leu Ala Thr Asn Arg Met
         115                 120                 125

Glu Pro Leu Ile Leu His Trp Ala Leu Ala Lys Asn Pro Gly Glu Trp
 130                 135                 140

Glu Ala Pro Pro Ser Ser Ile Val Pro Ser Gly Ser Thr Val Leu Asp
 145                 150                 155                 160

Lys Ala Cys Glu Thr Ser Phe Gly Glu Ser Glu Leu Asp Gly Leu Gln
             165                 170                 175

Tyr Gln Val Val Glu Ile Glu Leu Asp Asp Gly Arg Tyr Lys Gly Met
             180                 185                 190

Pro Phe Val Leu Arg Arg Gly Glu Thr Trp Ile Lys Asn Asn Asp Ser
         195                 200                 205

Asp Phe Tyr Leu Asp Phe Asn Thr Lys Val Thr Lys Ser Lys Asp
         210                 215                 220

Thr Gly Asp Ala Gly Lys Gly Thr Ala Lys Asp Phe Leu Glu Arg Ile
225                 230                 235                 240

Ala Asp Leu Glu Glu Asp Ala Gln Arg Ser Phe Met His Arg Phe Asn
             245                 250                 255

Ile Ala Ala Asp Leu Val Asp Gln Ala Arg Asp Ala Gly Leu Leu Gly
         260                 265                 270

Ile Val Gly Leu Phe Val Trp Ile Arg Phe Met Ser Thr Arg Gln Leu
         275                 280                 285

Ile Trp Asn Lys Asn Tyr Asn Val Lys Pro Arg Glu Ile Ser Gln Ala
 290                 295                 300

Gln Asp Arg Phe Thr Asp Asp Leu Glu Asn Met Tyr Lys Ser Tyr Pro
305                 310                 315                 320

Gln Tyr Arg Glu Ile Leu Arg Met Leu Leu Ser Ala Val Gly Arg Gly
             325                 330                 335

Gly Glu Gly Asp Val Gly Gln Arg Ile Arg Asp Glu Ile Leu Val Ile
             340                 345                 350

Gln Arg Asn Asn Asp Cys Lys Gly Gly Ile Met Glu Glu Trp His Gln
         355                 360                 365

Lys Leu His Asn Asn Thr Ser Pro Asp Asp Val Val Ile Cys Gln Ala
         370                 375                 380

Ile Ile Asp Tyr Ile Lys Ser Asp Phe Asp Ile Asn Val Tyr Trp Asp
385                 390                 395                 400

Thr Leu Asn Lys Asn Gly Ile Thr Lys Glu Arg Leu Leu Ser Tyr Asp
             405                 410                 415

Arg Ala Ile His Ser Glu Pro Lys Phe Arg Ser Asp Gln Lys Glu Gly
         420                 425                 430

Leu Leu Arg Asp Leu Gly Asn Tyr Met Arg Ser Leu Lys Ala Val His
         435                 440                 445
```

-continued

```
Ser Gly Ala Asp Leu Glu Ser Ala Ile Ala Thr Cys Met Gly Tyr Lys
        450                 455                 460

Ser Glu Gly Glu Gly Phe Met Val Gly Val Gln Ile Asn Pro Val Asn
465                 470                 475                 480

Gly Leu Ser Ser Gly Phe Pro Asp Leu Leu Gln Phe Val Leu Asp His
                485                 490                 495

Val Glu Asp Lys Ser Ala Glu Pro Leu Leu Glu Gly Leu Leu Glu Ala
                500                 505                 510

Arg Val Glu Leu Arg Pro Leu Leu Thr Gly Ser Ser Glu Arg Leu Lys
        515                 520                 525

Asp Leu Ile Phe Leu Asp Ile Ala Leu Asp Ser Thr Phe Arg Thr Ala
        530                 535                 540

Val Glu Arg Ser Tyr Glu Leu Asn Asp Ala Ala Pro Glu Lys Ile
545                 550                 555                 560

Met Tyr Phe Ile Ser Leu Val Leu Glu Asn Leu Ala Leu Ser Thr Asp
                565                 570                 575

Asp Asn Glu Asp Ile Leu Tyr Cys Leu Lys Gly Trp Asn Arg Ala Met
                580                 585                 590

Asp Met Val Lys Gln Lys Asp Asp Gln Trp Ala Leu Tyr Ala Lys Ala
        595                 600                 605

Phe Leu Asp Arg Thr Arg Leu Ala Leu Ala Ser Lys Gly Glu Gln Tyr
        610                 615                 620

Tyr Asn Met Met Gln Pro Ser Ala Glu Tyr Leu Gly Ser Leu Leu Asn
625                 630                 635                 640

Val Glu Glu Trp Ala Val Asp Ile Phe Thr Glu Glu Val Ile Arg Gly
                645                 650                 655

Gly Ser Ala Ala Thr Leu Ser Ala Leu Leu Asn Arg Phe Asp Pro Val
                660                 665                 670

Leu Arg Asn Val Ala His Leu Gly Ser Trp Gln Val Ile Ser Pro Val
        675                 680                 685

Glu Val Thr Gly Tyr Ile Val Val Asp Lys Leu Leu Ser Val Gln
690                 695                 700

Asn Lys Thr Tyr Asp Lys Pro Thr Ile Leu Val Ala Lys Ser Val Lys
705                 710                 715                 720

Gly Glu Glu Glu Ile Pro Asp Gly Val Gly Val Ile Thr Pro Asp
                725                 730                 735

Met Pro Asp Val Leu Ser His Val Ser Val Arg Ala Arg Asn Cys Lys
                740                 745                 750

Val Leu Phe Ala Thr Cys Phe Asp Pro Asn Thr Leu Ser Glu Phe Gln
        755                 760                 765

Gly His Glu Gly Lys Val Phe Ser Phe Lys Thr Thr Ser Ala Asp Val
770                 775                 780

Thr Tyr Arg Glu Val Ser Asp Ser Glu Leu Met Gln Ser Ser Ser Ser
785                 790                 795                 800

Asp Ala Gln Gly Gly Glu Ala Ile Pro Ser Leu Ser Leu Val Lys Lys
                805                 810                 815

Lys Phe Leu Gly Lys Tyr Ala Ile Ser Ala Glu Glu Phe Ser Asp Glu
        820                 825                 830
```

-continued

```
Met Val Gly Ala Lys Ser Arg Asn Ile Ala Tyr Leu Lys Gly Lys Val
            835                 840                 845

Pro Ser Trp Val Gly Ile Pro Thr Ser Val Ala Ile Pro Phe Gly Thr
    850                 855                 860

Phe Glu Lys Ile Leu Ser Asp Glu Thr Asn Lys Glu Val Ala Gln Asn
865                 870                 875                 880

Ile Gln Met Leu Lys Gly Arg Leu Ala Gln Glu Asp Phe Ser Ala Leu
                885                 890                 895

Gly Glu Ile Arg Lys Thr Val Leu Asn Leu Thr Ala Pro Thr Gln Pro
                900                 905                 910

Val Lys Glu Leu Lys Glu Lys Met Leu Ser Ser Gly Met Pro Trp Pro
            915                 920                 925

Gly Asp Glu Ser Asp His Arg Trp Glu Gln Ala Trp Met Ala Ile Lys
    930                 935                 940

Lys Val Trp Ala Ser Lys Trp Asn Glu Arg Ala Tyr Phe Ser Thr Arg
945                 950                 955                 960

Lys Val Lys Leu Asp His Glu Tyr Leu Ser Met Ala Val Leu Val Gln
                965                 970                 975

Glu Ile Val Asn Ala Asp Tyr Ala Phe Val Ile His Thr Asn Pro
                980                 985                 990

Ser Ser Gly Asp Ser Ser Glu Ile Tyr Ala Glu Val Val Lys Gly Leu
            995                 1000                1005

Gly Glu Thr Leu Val Gly Ala Tyr Pro Gly Arg Ala Met Ser Phe
    1010                1015                1020

Val Cys Lys Lys Asp Asp Leu Asp Ser Pro Lys Val Leu Gly Tyr
    1025                1030                1035

Pro Ser Lys Pro Ile Gly Leu Phe Ile Lys Arg Ser Ile Ile Phe
    1040                1045                1050

Arg Ser Asp Ser Asn Gly Glu Asp Leu Glu Gly Tyr Ala Gly Ala
    1055                1060                1065

Gly Leu Tyr Asp Ser Val Pro Met Asp Val Glu Asp Glu Val Val
    1070                1075                1080

Leu Asp Tyr Thr Thr Asp Pro Leu Ile Thr Asp Ser Gly Phe Arg
    1085                1090                1095

Asn Ser Ile Leu Ser Ser Ile Ala Arg Ala Gly His Ala Ile Glu
    1100                1105                1110

Glu Leu Tyr Gly Ser Pro Gln Asp Val Glu Gly Val Val Lys Asp
    1115                1120                1125

Gly Lys Ile Tyr Val Val Gln Thr Tyr His Arg Cys Asn Met Tyr
    1130                1135                1140

Val Tyr Ala Ala Gln Val Val Glu
    1145                1150
```

NUCLEIC ACID MOLECULES FROM WHEAT ENCODING AN R1-PROTEIN, AND TRANSGENIC PLANT CELLS AND PLANTS COMPRISING THE NUCLEIC ACID MOLECULES

CROSS-REFERENCE TO RELATED APPLICATIONS

The present application is a divisional of application Ser. No. 09/590,101, filed Jun. 8, 2000, which claims priority to DE 199 26 771.5, filed Jun. 11, 1999.

Each of the foregoing applications, and each document cited or referenced in each of the foregoing applications and during the prosecution of each of the foregoing applications ("application cited documents"), and each document referenced or cited in each of the application cited documents, and each document cited or referenced in this application ("herein cited documents") and each document cited or referenced in each of the herein cited documents, as well as all documents of Applicants during prosecution of each of the foregoing applications, are all hereby incorporated herein by reference.

FIELD OF THE INVENTION

The present invention relates to nucleic acid molecules encoding R1-protein from wheat and derivatives and parts thereof, said R1-protein, processes for the production of said R1-protein, transgenic plant cells and plants comprising said nucleic acid molecules, the transgenic plant cells and plants comprising said nucleic acid molecule, and the modified starch obtainable from said transgenic plant cells and plants.

BACKGROUND OF THE INVENTION

The polysaccharide starch constitutes one of the most important storage substances in plants. Starch is widely used for the production of foodstuffs and plays also a significant role as a regenerative raw material in manufacturing of industrial products. In order to use starches in many different technical areas a large variety of optionally modified starches is required in order to meet the varying needs of the processing industry.

Although starch consists of a chemically homogeneous basic component, namely glucose, it does not constitute a homogeneous raw material. It is a complex mixture of molecules which differ in their degree of polymerization and degree of branching of the glucose chains: Amylose-type starch is a basically unbranched polymer consisting of α-1,4-glycosidically branched glucose molecules, whereas amylopectin-type starch is a mixture of branched glucose chains, comprising additionally α-1,6-glycosidic interlinkings.

The molecular structure of starch mainly depends on its degree of branching, the amylose/amylopectin ratio, the average chain-length, chain lenght distribution, and degree of phosphorylation, further determining the functional properties of the starch and the aequous solutions thereof. Important functional properties of the starch, resp., the aequous solutions thereof are, e.g., solubility, tendency to retrogradation, capability of film formation, viscosity, pastification (binding and gluing) properties, and cold resistance. Additionally, the size of the starch granules may also determine the suitability of the starch for particular applications.

Since starch is often adapted by chemical and/or physical modification in order to meet the requirements of industry, there is a great need for the provision of modified starches which would render plant cells or plant parts containing modified starch more suitable for industrial processing, e.g., the production of foodstuff or technical products. Therefore, it is desired to avoid chemical and/or physical modification, which is time-consuming and expensive and to provide plants which synthesize a starch which meets more closely the demands of the starch processing industry.

Conventional methods for the preparation of modified plants which produce modified products, e.g., by classical breeding and/or the production of mutants, are limited to the use of homologous genes and are not always satisfying. Particularly in wheat, it is difficult to prepare a stable mutant by classical breeding due to the polyploidity of wheat (tetra- or hexaploidity). However, a wheat mutant producing waxy-type starch (amylose-free starch) was recently achieved by breeding methods (Nakamura et al., Mol. Gen. Genet. 248 (1995), 253–259).

A further alternative is the preparation of transgenic plants which comprise nucleic acid molecules suitable to modify plant starch metabolism in order to synthesize a modified starch. Such plants are produced by means of recombinant molecular biological techniques and the introduction of homologous and/or heterologous nucleic acid molecules (e.g., coding regions, regulatory elements, introns), which interfere in starch metabolism. However, the application of recombinant molecular biological techniques requires the availability of suitable nucleic acid which participate directly or indirectly (e.g., cosuppression, anti-sense-technology, generation of protein or ribozyme) in starch metabolism or starch biosynthesis (i.e., synthesis, modification and/or degradation of starch) with respect to quantity and/or quality of the starch.

Numerous genes are involved in starch metabolism. Therefore, a large number of genes encoding, e.g., branching enzymes, debranching enzymes, isoamylases, starch synthetases, ADP-glucose-pyrophosphorylases, have been used to modify starch metabolism in plants.

R1 proteins are involved in starch metabolism, especially with respect to the degree of phosphorylation of the starch and therefore, suitable to modify starch synthesis. In particular, R1-proteins and genes encoding R1-proteins derived from a number of plant species are known, i.e., potato from WO 97/11188-A1 and Lorberth et al., Nature Biotechnology 16 (1998), 473–477), maize from WO 98/27212-A1, rice from Sakaki et al., EMBL database entry Accession No. C 71741 (1997-09-19), and *arabidopsis*, ginger, mosses, cattail (*Typha latifolia*), and soybean from WO 99/53072-A1.

However, the presence of an R1-protein in wheat plants was not shown, corresponding nucleic acid molecules were not identified. Furthermore, the known nucleic acid molecules encoding R1-proteins are not always satisfying or suitable for the genetic engeneering or the in vivo mutagenesis of wheat plants in order to modify wheat starch biosynthesis and/or metabolism.

OBJECTS AND SUMMARY OF THE INVENTION

Therefore, the problem to be solved by the present invention is to provide nucleic acid molecules encoding R1-protein derived from wheat and methods which allow the modification of starch metabolism in plants, especially in wheat plants in order to provide a modified starch, which differs from starch naturally synthesized with respect to its physical and/or chemical properties, especially wheat starch, exhibiting improved features, in particular for application in food and/or non-food industry.

These problems are solved by the embodiments of the present invention as claimed.

DETAILED DESCRIPTION

Therefore, the present invention relates to nucleic acid molecules encoding R1-protein comprising an amino acid sequence according to Seq. ID No. 2 and Seq. ID No. 10 or derivative or part thereof according to the cDNA insert of plasmid pTaR1-11 (DSM No. 12810) and plasmid RS26-88 (DSM No. 13511). Said R1-protein of the invention is involved in starch metabolism and is involved directly or indirectly in starch biosynthesis of wheat with respect to the degree of phosphorylation.

Within the meaning of the present invention, the term "derivative" regarding the R1-protein (polypeptide, amino acid sequence) of the invention encompasses a polypeptide derived from Seq ID No. 2 comprising about at least 60–79 amino acid radicals, preferably at least 80, more preferred at least 90, in particular at least 100, and most preferably about 101–111 amino acid radicals selected from the group of amino acid radicals consisting of 1E, 2V, 3V, 5G, 6L, 7G, 8E, 9T, 10L, 11V, 12G, 13A, 14Y, 15P, 16G, 17R, 18A, 20S, 21F, 23C, 24K, 25K, 27D, 28L, 30S, 31P, 34L, 35G, 36Y, 37P, 38S, 39K, 40P, 41I, 42G, 43L, 44F, 45I, 48S, 49I, 50I, 51F, 52R, 53S, 54D, 55S, 56N, 57G, 58E, 59D, 60L, 61E, 62G, 63Y, 64A, 65G, 66A, 67G, 68L, 69Y, 70D, 71S, 72V, 73P, 74M, 75D, 77E, 80V, 81V, 83D, 84Y, 87D, 88P, 89L, 90I, 92D, 95F, 96R, 99I, 100L, 101S, 103I, 104A, 105R, 106A, 107G, 108H, 109A, 110I, 111E, 112E, 113L, 114Y, 115G, 116S, 117P, 118Q, 119D, 121E, 122G, 123V, 124V, 126D, 127G, 128K, 129I, 130Y, 131V, 132V, 133Q, and 134T and comprising at least 1, preferably 2, and more preferred 3 of the amino acid radicals selected from the group consisting of 76V, 93S, and 97N of the amino acid radicals (hereinbefore indicated by single letter code) as specified in Seq ID No. 2.

Within the meaning of the present invention, the term "part" regarding the R1-protein (polypeptide, amino acid sequence) of the invention encompasses a poly- or oligopeptide consisting of about at least 10–19, preferably at least 20, more preferably at least 40, in particular preferably at least 80, and most preferably about 100–140 of the amino acid radicals of the R1-protein or derivative thereof according to the invention.

The present invention further relates to nucleic acid molecules comprising a nucleic acid molecule derived from Seq. ID No. 1 and Seq. ID No. 9 or derivatives or parts thereof, the 672 bp EcoR I/Kpn I insert of plasmid pTa R1-11 (DSM No. 12810) or derivatives or parts thereof, in particular the coding region (nucleotides 1–449) of Seq. ID No. 1 or derivatives or parts thereof, especially the coding region of the insert of plasmid pTa R1-11 (DSM No. 12810) and the coding region of plasmid RS26-88 (DSM No. 13511) or derivatives or parts thereof.

Within the meaning of the present invention, the term "derivative" regarding the nucleic acid molecule (nucleotide sequence, or polynucleotide) of the invention encompasses a polynucleotide comprising about at least 150–209 nucleotides, preferably at least 210, more preferred at least 240, in particular at least 270, and most preferably about 280–294 nucleotides selected from the group of nucleotides consisting of (a) 1C, 3G, 4A, 6G, 7T, 8G, 9G, 10T, 12A, 15G, 16G, 18C, 19T, 20T, 21G, 22G, 24G, 25A, 27A, 28C, 30C, 31T, 33G, 34T, 36G, 37G, 38A, 39G, 40C, 42T, 43A, 44T, 45C, 46C, 48G, 49G, 51C, 52G, 53T, 54G, 55C, 58T, 59G, 60A, 61G, 63T, 64T, 67T, 69T, 70G, 72A, 73A, 75A, 76A, 77A, 79A, 81G, 82A, 84C, 85T, 88A, 89C, 90T, 91C, 92T, 93C, 94C, 97A, 100T, 103T, 105G, 106G, 107T, 108T, 109A, 110C, 111C, 112C, 114A, 115G, 116C, 117A, 118A, 120C, 121C, 123A, 124T, 126G, 127G, 129C, 130T, 132T, 133T, 134C, 135A, 136T, 137A, 138A, 144T, 145C, 147A, 148T, 149C, 150A, 151T, 152C, 153T, 154T, 155C, 156C, 157C, 159T, 160C, 162G, 163A, 165T, 166C, 168A, 169A, 171G, 172G, 174G, 175A, 177G, 178A, 181T, 182G, 183G, 184A, 185A, 186G, 187G, 188T, 189T, 190A, 192G, 193C, 195G, 196G, 198G, 199C, 201G, 202G, 205T, 207T, 208A, 210G, 211A, 213A, 214G, 215T, 216G, 217T, 219C, 220C, 222A, 223T, 224G, 225G, 226A, 227T, 228G, 230G, 231G, 232A, 234G, 235A, 238A, 240G, 241T, 242T, 243G, 244T, 245A, 247T, 249G, 250A, 252T, 253A, 256C, 259C, 261G, 262A, 263C, 264C, 265C, 268T, 270A, 271T, 276G, 277A, 281T, 285T, 286T, 287C, 288C, 289G, 295C, 296A, 297A, 298T, 299C, 300C, 301T, 303T, 304C, 306A, 308C, 309A, 310T, 312G, 313C, 315C, 316G, 318G, 319C, 320T, 321G, 322G, 324C, 325A, 327G, 328C, 330A, 331T, 332C, 333G, 334A, 335G, 336G, 337A, 338G, 339C, 340T, 342T, 343A, 344T, 345G, 346G, 348T, 349C, 351C, 352C, 354C, 355A, 357G, 358A, 361T, 363G, 364A, 365G, 366G, 367G, 369G, 370T, 371A, 372G, 373T, 374G, 375A, 377G, 378G, 379A, 380T, 381G, 382G, 384A, 385A, 387A, 388T, 390T, 391A, 393G, 394T, 396G, 397T, 399C, 400A, 401G, 402A, 403C, 404A, 406A, 407C, 408C, 409A, 410C, 411A, 412G, 413A, 414T, 415G, 416T, and 419T as specified in Seq. ID No. 1, and (b) comprising about at least 15–19 nucleotides, preferably at least 20, more preferred at least 25, in particular at least 27, and most preferably about 30–32 nucleotides selected from the group consisting of 17A, 23A, 50C, 56C, 65C, 68G, 71T, 104G, 113T, 143G, 159C, 161A, 167T, 191C, 203G, 206G, 218C, 221T, 229T, 233A, 248C, 251C, 257G, 269C, 272C, 279T, 280C, 290G, 326C, 341C, 347G, 350A. 353A, 359T, 383G, 392C, and 405T as specified in Seq. ID No. 1.

It is expressly stated that the numbering of the elements of the sequences (on one hand nucleic acid sequence and on the other amino acid sequence) shall not be understood as a fixed or limiting definition. The numbering shall merely provide the information of the positions of the sequence elements to each other in relative terms and is therefore a reference.

Furthermore, the term "derivative" regarding the nucleic acid molecule encoding an R1-protein according to the invention encompasses a nucleic acid molecule which is different from Seq. ID No. 1 and/or Seq ID No. 9 by addition, deletion, insertion or recombination of one or more nucleotides and fulfills the definition as given above under (b).

Additionally, the term "derivative" regarding the nucleic acid molecule encoding an R1-protein according to instant invention encompasses a complementary or reverse complementary polynucleotide of the nucleic acid molecule according to the invention or parts thereof. Furthermore, the term "derivative" regarding the nucleic acid molecule encoding an R1-protein according to instant invention comprises a polynucleotide hybridizing with the nucleic acid molecule according to the invention or parts thereof, which fulfills the definition as given above under (b).

The term "hybridization" denotes, for the purposes of the present invention, a hybridization under conventional hybridization conditions, preferably under stringent conditions as described, for example, by Sambrook et al., Molecular Cloning, A Laboratory Manual, 2nd Edition (1989) Cold Spring Harbor Laboratory Press, Cold Spring Harbor, N.Y.).

Especially preferably, "specific hybridization" means the following conditions:

Hybridization buffer: 2×SSC; 10× Denhardt solution (Ficoll 400+PEG+BSA; ratio 1:1:1); 0.1% SDS; 5 mM EDTA; 50 mM $Na_2HPO_4$; 250 µg/ml herring sperm DNA; 50 µg/ml tRNA; or 0.25 M sodium phosphate buffer pH 7.2; 1 mM EDTA; 7% SDS at a

| Hybridization temperature of | T = 55 to 68 °C., |
|---|---|
| Wash buffer: | 0.2 × SSC; 0.1% SDS and |
| Wash temperature: | T = 40 to 68° C. |

The molecules which hybridize with the nucleic acid molecules according to the invention or with the nucleic acid molecules to be suitably employed according to the invention also encompass parts, derivatives and allelic variants of the nucleic acid molecules according to the invention or the nucleic acid molecule to be suitably employed in accordance with the invention.

The term "derivative" means, within the context of the present invention, that the sequences of these molecules differ from the sequences of the nucleic acid molecules according to the invention or to be suitably employed in accordance with the invention in one or more positions and exhibit a high degree of homology to these sequences. Homology means a sequential identity of at least 60%, preferably over 70%, and especially preferably over 85%, in particular over 90% and very especially preferably over 95%. The deviations relative to the nucleic acid molecules according to the invention or to the nucleic acid molecules to be suitably employed in accordance with the invention may have originated by means of one or more deletions, substitutions, insertions (addition) or recombinations.

Furthermore, homology means that a functional and/or structural equivalence exits between the nucleic acid molecules in question and the proteins encoded by them. The nucleic acid molecules which are homologous to the molecules according to the invention or to the molecules to be suitably employed in accordance with the invention and which constitute derivatives of these molecules are, as a rule, variations of these molecules which constitute modifications which exert the same, a virtually identical or a similar biological function. They may be naturally occurring variations, for example sequences from other plant species, or mutations, it being possible for these mutations to have occurred naturally or to have been introduced by directed mutagenesis. The variations may further be synthetic sequences. The allelic variants may be naturally occurring variants or else synthetic variants or variants generated by recombinant DNA technology.

The term "part" regarding the nucleic acid molecule encoding an R1-protein according to instant invention encompasses a poly- or oligonucleotide consisting of about at least 30–99, preferably at least 100, more preferably at least 200, in particular at least 300, and most preferably at least 400 of the nucleotides of the nucleic acid molecule encoding an R1-protein or derivative thereof according to the invention. The term "part" is not limited to portions of the nucleic acid molecules which are long enough to encode a functionally active portion of the R1-protein as described.

In a preferred embodiment of instant invention, the terms "derivative" and/or "part" according to instant invention encompass a polynucleotide, resp., poly- or oligopeptide as defined above, which exhibits functional and/or structural equivalence of the R1-gene (i.e., the nucleic acid molecule encoding R1-protein), resp., R1-protein derived from wheat. The the term "functional and/or structural equivalence" generally means the same, an equivalent or a similar function of the resp. molecule of the invention, especially biological function. The term "part" is, however, not limited to portions of the said nucleic acid molecule, which are sufficient to encode a funcionally active portion of the said protein.

The R1-proteins encoded by the nucleic acid molecules according to the invention may exhibit certain common characteristics, e.g., enzyme activity, molecular weight, immunologic reactivity, conformation, mobility in gel electrophoresis, chromatographic characteristics, sedimentation coefficients, solubility, spectroscopic properties, stability, pH-optimum and/or temperature-optimum of the enzymatic activity, etc.

The nucleic acid molecule of the invention may be isolated from, e.g., natural sources, prepared by methods of genetic engineering or molecular biology (e.g., PCR) or produced by means of chemical synthesis. The nucleic acid molecule of the invention is preferably a DNA or RNA molecule, e.g., a cDNA or genomic DNA molecule. Optionally, the nucleic acid molecule of the invention comprises one or more intervening sequences (introns).

In another preferred embodiment the nucleic acid molecule of the invention comprises one or more regulatory elements that ensure the transcription and synthesis of an RNA molecule in a prokaryotic and/or eukaryotic cell, preferably in a plant cell.

The nucleic acid molecule according to the invention is suitable in order to modify starch biosynthesis/metabolism in a cell, preferably in a plant cell by means of sense expression of the nucleic acid molecules of the invention, antisense expression of the nucleic acid molecules of the invention, expression of a suitable ribozyme, cosuppression or in vivo mutagenesis.

Therefore, the invention relates also to the use of the nucleic acid molecule of the invention, in particular a DNA molecule, which allows the synthesis of a translatable or a non-translatable mRNA molecule (sense- or anti-sense-, co-suppression effect or ribozyme) in a cell or a plant cell which modifies the R1-protein expression level.

Generally, the use of the nucleic acid molecules of the invention is suitable in any plant species. However, monocotyledonous and dicotyledonous plants are preferred, in particular crop plants and most preferred starch-storing plants, e.g., rye, barley, oats, wheat, millet, sago, rice, maize, peas, wrinkled peas, cassava, potato, tomato, oilseed rape, soy bean, hemp, flax, sunflower, cow-pea, arrowroot, clover, ryegrass, or alfalfa, in particularly potato, maize, rice or wheat plants.

The method of co-suppression is well known to the person skilled in the art (Jorgensen, Trends Biotechnol. 8 (1990), 340–344, Niebel et al., Curr. Top. Microbiol. Immunol. 197 (1995), 91–103, Flavell et al., Curr. Top. Microbiol. Immunol. 197 (1995), 43–56, Palaqui & Vaucheret, Plant. Mol. Biol. 29 (1995), 149–159. Vaucheret et al., Mol. Gen. Genet. 248 (1995), 311–317 and de Borne et al., Mol. Gen. Genet 243 (1994), 613–621.

In a further embodiment the present invention relates to a DNA molecule encoding an RNA molecule exhibiting ribozyme activity which specifically cleaves transcripts of the DNA molecule of the invention. Ribozymes are catalytically active RNA molecules capable of cleaving RNA molecules and specific target sequences. By means of recombinant DNA techniques it is possible to determine the specificity of a ribozyme with respect to the nucleic acid molecule of the invention. In order to prepare a DNA molecule encoding a ribozyme which specifically cleaves a transcript of a DNA molecule of the invention, e.g., a DNA sequence (DNA molecule) encoding a catalytic domain of a ribozyme is bilaterally linked to a DNA sequence of the invention. A nucleic acid sequence encoding the catalytic domain is, e.g., the catalytic domain of the satellite DNA of the SCMO virus (Davies et al., Virology 177 (1990), 216–224) or the satellite DNA of the TobR virus (Steinecke et al., EMBO J. 11 (1992), 1525–1530; Haseloff and Gerlach, Nature 334 (1988), 585–591). The DNA sequence flanking the catalytic domain is preferably the DNA molecule of the invention or part thereof, which shall serve as a target. The general principle of the expression of ribozymes and the method is described in EP-B1 0 321 201. The expression of ribozymes in plant cells is further described in Feyter et al. (Mol. Gen. Genetic. 250 (1996), 329–338).

A reduction of the activity of the R1-protein of the invention in a plant cell can also be achieved by the method of "in vivo mutagenesis". Hereby, a hybrid RNA/DNA oligonucleotide (chimeroplast) is introduced into a cell (Kipp et al., Poster Session at the 5th International Congress of Plant Molecular Biology, Sep. 21 to 27, 1997, Singapore; Dixon and Arntzen, meeting report on "Metabolic Engineering in Transgenic Plants" Keystone Symposia, Copper Mountain, Colo., USA, TIBTECH 15 (1997), 441–447; WO 95/15972-A1; Kren et al., Hepatology 25 (1997), 1462–1468; Cole-Strauss et al., Science 273 (1996), 1386–1389).

Therefore, yet another object of the invention is a plant, preferably a wheat plant, exhibiting an altered activity of the R1-protein according to the invention obtainable by in vivo mutagenesis.

Furthermore, the invention relates to a vector, especially a plasmid, cosmid, virus, bacteriophage and the like, suitable in genetic engineering, comprising a nucleic acid molecule (e.g., DNA and/or RNA) of the invention, in particular a vector suitable in genetic engeneering of bacteria and/or plants. The term "vector" means a suitable vehicle known to the skilled artisan, which allows the targeted transfer of single or double-stranded nucleic acid molecules into a host cell, e.g., a DNA or RNA virus or virus fragment, a plasmid which is suitable for the transfer of a nucleic acid molecule into a cell in the presence or absence of regulatory elements, metal particles as employed, e.g., in the particle-gun method, but also a nucleic acid molecule which can be directly introduced into a cell by chemical and/or physical methods.

In a further embodiment the invention relates to a transgenic host cell, which is transformed and/or recombinantly manipulated by a nucleic acid molecule or a vector according to the invention, in particular a transgenic prokaryotic or eukaryotic cell, and more preferably a transgenic bacterial or a plant cell. The transgenic host cell according to the invention, especially the transgenic bacterial or plant cell contains one or more nucleic acid molecules of the invention, which are stably integrated into the genome of said cell, preferably not at the homologous genomic locus, resp., not at the location of the naturally occuring gene within the genome. The transgenic cells according to the invention may be identified by Southern Blot, Northern Blot and/or Western Blot analysis.

Additionally, the present invention relates to a transgenic cell, which is derived from the transgenic host cell of the invention and/or the descendants thereof containing a nucleic acid molecule or a vector according to the invention.

By provision of the nucleic acid molecule and/or the vector of the invention a transgenic plant cell or plant is prepared by means of recombinant DNA techniques comprising a nucleic acid molecule and/or a vector according to the invention, in particular a monocotyledonous or dicotyledonous plant cell or plant, preferably a crop plant cell or a plant, in particular a plant cell or plant selected from the group consisting of a potato, maize, oat, rye, barley, wheat, pea, rice, millet, wrinkled peas, cassava, sago, tomato, oilseed rape, soy bean, hemp, flax, sunflower, cow-pea, arrowroot, clover, ryegrass, alfalfa, and maniok.

The transgenic plant cell or plant of the invention synthesizes a modified starch which differs from the starch synthesized in a wildtype (non-transformed) plant with respect to structure and/or physical and/or chemical properties. By the methods of genetic engeneering and/or molecular biology, a vector and/or a nucleic acid molecule of the invention is introduced into a plant cell, preferably linked to one or more regulatory elements, which ensure transcription and/or translation in said plant cell. Optionally, the resulting transgenic plant cell is subsequently regenerated to a whole plant.

Therefore, the present invention relates to a transgenic plant cell, in particular a monocotyledonous or dicotyledonous plant cell, preferably, a potato, maize, oat, rye, barley, wheat, pea, rice, millet, wrinkled peas, cassava, sago, tomato, oilseed rape, soy bean, hemp, flax, sunflower, cow-pea, arrowroot, clover, ryegrass, alfalfa, or maniok cell, in particular potato, wheat, maize or rice cell, comprising a nucleic acid molecule and/or a vector according to the invention.

The invention relates also to a process for the preparation of a transgenic host cell, preferably, a plant cell comprising the step of introducing a nucleic acid molecule and/or a vector of the invention into the genome of a host cell which is a procaryotic or eucaryotic cell, preferably, into the genome of a plant cell. Preferably, said cell contains a nucleic acid molecule which is linked to one or more regulatory elements which ensure transcription and/or translation in said cell. Suitable regulatory elements are preferably homologous or heterologous with respect to the nucleic acid molecule of the invention.

In another embodiment, the invention relates to a transgenic plant cell wherein the presence of a (homologous or optionally, heterologous) nucleic acid molecule of the invention leads directly or indirectly to the expression of the R1-protein of the invention or, alternatively, to the inhibition of the expression of one or more endogenous genes encoding an R1-protein. Preferably, the transgenic plant cell comprises a nucleic acid molecule which is selected from the group consisting of:

(a) a nucleic acid molecule of the invention, preferably a DNA molecule, which is transcribed into sense-RNA, which leads to the expression of an R1-protein of the invention;

(b) a nucleic acid molecule molecule of the invention, preferably a DNA molecule, which is transcribed into antisense-RNA which leads to the reduction (inhibition) of the expression of one or more endogenous genes encoding an R1-protein;

(c) a nucleic acid molecule molecule of the invention, preferably a DNA molecule, which is transcribed into a cosuppression-RNA (sense RNA) which leads to a reduction (inhibition) of the expression of one or more endogenous genes encoding an R1-protein;

(d) a nucleic acid molecule molecule of the invention, preferably a DNA molecule, which is transcribed into a ribozyme which specifically cleaves a transcript of one or more endogenous genes encoding an R1-protein; and (e) a nucleic acid molecule of the invention which is introduced by in vivo mutagenesis, which modifies one or more endogenous genes encoding an R1-protein, hereby modifying starch metabolism/biosynthesis in said cell.

If the modification of starch metabolism in plants is achieved by means of an antisense effect, the DNA molecule of the invention is linked in antisense orientation with one or more regulatory elements ensuring the transcription and/or translation in a plant cell, optionally comprising one or more intron(s) of a corresponding genomic sequence of the polynucleotide to be expressed. The antisense RNA should exhibit a minimum of about 15–25 nucleotides, preferably at least about 50–100 nucleotides and most preferably at least about 200–1000 nucleotides.

In a further embodiment the decrease in the amount of an R1-protein in the transgenic plant cell is achieved by a ribozyme comprising a nucleic acid molecule of the invention. In order to express said ribozyme molecule in a transgenic plant cell of the invention, a DNA molecule encoding said ribozyme is linked to one or more regulatory elements which ensure transcription and/or translation.

By means of methods well known to the skilled person, the transgenic plant cell can be regenerated to a whole plant. The transgenic plant comprising a transgenic plant cell of the invention which is obtainable by regenerating the transgenic plant cell of the invention and the process for the preparation of said transgenic plant are also subject-matter of the present invention.

The transgenic plant of the invention is a monocotyledonous or dicotyledonous plant, preferably a crop plant, in particular a rye, barley, oat, rice, wheat, millet, sago, maize, pea, wrinkled pea, cassava, potato, tomato, maniok, oil seed rape, soy bean, hamp, flax, sunflower, cow-pea, white clover, ryegrass, alfalfa or arrowroot plant, most preferred a maize, wheat, rice, or potato plant.

Further the present invention relates to the propagation material, seed, organs, and parts of the plants of the invention.

The present invention also relates to a process for the production of starch comprising the step of introducing a transgenic plant cell, plant and/or part of a plant according to the invention into a process for the production/extraction of starch.

The present invention further relates to a process for the production of modified starch comprising the step of introducing a starch according to the invention into a process of chemical and/or physical modification/traetment of starch.

Processes for starch extraction from plants, plant cells, or parts thereof are well known in the art. Such processes are described, for example, in Eckhoff et al. (Cereal Chem. 73 (1996), 54–57). Extraction of maize starch is achieved by, e.g., "wet-milling". Other methods for starch extraction from various plants are described, e.g., in Starch: Chemistry and Technology (eds.: Whistler, BeMiller and Paschall (1994) 2nd Edition, Academic Press Inc. London LTD; ISBN 0-12-746270-8; Chapter XII, page 417–468: Corn and Sorghum Starches: Production; by Watson, S. A.; Chapter XIII, page 469–479: Tapioca, Arrowroot and Sago Starches: Production by Corbishley and Miller; Chapter XIV, page 479–490: Potato Starch: Production and Uses; by Mitch; Chapter XV, page 491–506: Wheat starch: Production, Modification and Uses; by Knight and Olson; and Chapter XVI, page 507–528: Rice starch: Production and Uses; by Rohwer and Klem). Means usually used in methods for the extraction of starches from plant materials are separators, decanters, hydroclones and different kinds of machines for drying the starch, e.g., spray drier or jet drier.

The present invention also relates to the modified starch obtainable from the transgenic plant cells, plants and/or parts of a plant of the invention, preferably from wheat. The transgenic cells or plants of the invention synthesize a modified starch which differs from a starch obtainable from non-transformed plants with respect to the degree of phosphorylation. In a specific embodiment of the invention, the starch according to the invention exhibits an increased phosphate content compared to a starch obtainable from corresponding non-transformed cells or plants. An increased phosphate content (phosphate-monoester content) means a starch containing about at least 10–30%, more preferably at least 30%, even more preferably at least 50%, and particularly preferred more than 100% up to about 1000–5000% increased phosphate content compared to the phosphate content of a starch obtainable from a corresponding non-transformed plant. In general, the percentage values refer to the glucose-6-phosphate (glu-6-P) content of wheat starch of about 0.3 nmol glu-6-P/mg starch determined, e.g., according to the method of Lim et al. Cereal Chem., (1994) 71, 448. Accordingly, the wheat starch according to instant invention comprises a glucose-6-phosphate content of at least 0.4 nmol/mg starch, preferably of at least 0.6 nmol/mg, more preferred at least 0.8 nmol/mg, in particular at least 1.0 nmol/mg, especially at least 1.5 nmol/mg, and most preferred at least 3.0 nmol/mg starch.

In another embodiment of the invention the starch of the invention exhibits a decreased phosphate content (phosphate-monoester content) of about at least 5–20%, preferably about at least 21–50%, even more preferably about 51–95% decreased phosphate content compared to the phosphate content of a starch obtainable from a corresponding non-transformed plant. Accordingly, the wheat starch according to instant invention exhibits a glucose-6-phosphate content of less than 0.2 nmol/mg starch, preferably less than 0.1 nmol/mg, more preferred less than 0.05 nmol/mg, in particular less than 0.02 nmol/mg, especially less than 0.01 nmol/mg, and most preferred less than 0.001 nmol/mg starch.

Another object of the invention is a method for the preparation of the R1-protein of the invention or derivative or part thereof comprising the steps of cultivating a transgenic host cell of the invention under conditions allowing for the expression of said R1-protein or derivative or part thereof and isolating said R1-protein or derivative or part thereof from said cells and/or the cultivating medium of said cells.

Furthermore, the invention relates to an R1-protein (R1-polypeptide) or derivative or part thereof encoded by the nucleic acid molecule of the invention obtainable by the method for the production of an R1-protein or derivative or part thereof according to the invention, preferably an R1-protein or derivative or part thereof derived from wheat, especially according to Seq. ID No. 2 and/or Seq. ID No. 10.

Within the present invention, the term "regulatory element which ensures transcription and/or translation" preferably has the meaning of a nucleic acid molecule (e.g., DNA and/or RNA) which allows for the initiation and/or termination of transcription in a cell, such as promoters, enhancers, terminators etc. The term "regulatory element which ensures transcription and/or translation" may also comprise a nucleic acid molecule which leads to a timely and/or locally (endosperm, root, tuber, leaf, stem, seed, fruit, apoplast, vacuole, cytosol, plastid, mitochondrium, lysosme) limited transcription within a plant/or plant cell or which is chemically inducible.

For the expression of the nucleic acid molecules of the invention in a plant cell any active promoter may be used. Said promoter may be homologous or heterologous with respect to the plant cell to be transformed, e.g., for constitutive expression the 35S promoter of the cauliflower mosaic virus (CaMV) (Odell et al., Nature 313 (1985), 810–812; Mitsuhara et al., Plant and Cell Physiology 37 (1996), 49–59) or the promoter construct described in WO 94/01571-A1. Suitable are also promoters which lead to a locally and/or timely limited expression determined/induced by endogenous and/or exogenous factors (e.g., WO 93/07279-A1), e.g., a limited expression with respect to a particular tissue or part of the plant (Stockhaus et al., EMBO J. 8 (1989), 2245–2251). Promoters which are active in the starch-storing part of the plant to be transformed are preferred. Preferred parts of plants are for the expression of the nucleic acid molecules of the invention, e.g., maize, wheat and rice grains or seeds and potato tubers and the like. For the transformation of potato the tuber-specific B33-promoter (Rocha-Sosa et al., EMBO J. 8 (1989), 23–29) may be used. Apart from promoters, DNA regions initiating transcription may also contain DNA sequences ensuring a further increase of transcription, such as the so-called enhancer-elements. For expression in plant cells, and in particular in wheat cells, the following promoters can be used: the 35S promoter (Odell et al. supra; Mitsuhara et al., supra), the ubiquitin promoter (U.S. Pat. No. 5,614,399, Christensen et al., Plant Mol. Biol. 18 (1992), 675–689; Takimoto et al., Plant Mol. Biol. 26 (1994), 1007–1012; Cornejo et al., Plant Mol. Biol. 23 (1993), 567–581; Toki et al., Plant Phys. 100 (1992), 1503–1507), glutelin promoter (Leisy et al., Plant Mol. Biol. 14 (1990), 41–50; Zheng et al., Plant J. 4 (1993), 357–366; Kononowicz et al., Joint annual meeting of The American Society of Plant Physiologists and The Canadian Society of Plant Pyhsiologists, Minneapolis, Minn., USA, Jul. 1 to Aug. 4, 1993, Plant Physiol. 102 (suppl.) (1993) 166; Zhao et al., Annual Meeting of the American Society of Plant Physiologists, Pittsburgh, Pa., USA, Aug. 1 to 5, 1992. Plant Physiol. 99 (1 Suppl.) (1992), 85; Yoshihara et al., FEBS Lett. 383 (1996), 213–218, the actin promoter (McElroy et al., Plant Cell 2 (1990), 163–171), cab-6 promoter (Plant and Cell Physiology 35 (1994), 773–778), RTBV promoter (Yin et al., Plant J. 12 (1997), 1179–1188), CVMV promoter (Verdaguer et al., Plant Mol. Biol. 31 (1996), 1129–1139), rab 16B promoter (Plant Physiol. 112 (1996), 483–491), promoter of the psbD-C operon (To et al., Plant and Cell Physiology 37 (1996), 660–666), Tpi promoter (Snowden et al., Plant Mol. Biol. 31 (1996), 689–692), Osgrpl promoter (Xu et al., Plant Mol. Biol. 28 (1995), 455–471, Ltp2 promoter (Kalla et al., Plant J. 6 (1994), 849–860), ADH1 promoter (Kyozuka et al., Mol. Gen. Genet. 228 (1991), 40–48) and LHCP promoter (EMBO J. 10 (1991), 1803–1808).

Furthermore, the term "regulatory element" also comprises a termination signal suitable to finalize the transcription and/or to add a poly-A-tail to the transcribed nucleic acid molecule. Examples for a termination signal are the 3'-nontranslatable regions comprising the polyadenylation signal of the nopaline synthase gene (NOS gene) or octopine synthase gene (Gielen et al., EMBO J. 8 (1989), 23–29) from agrobacteria, the 3'-nontranslatable region of the gene of the storage protein from soy bean or small subunit of ribulose-1,5-biphosphate-carboxylase (ssRUBISCO). Optionally, the term "regulatory element" comprises a nucleic acid molecule which ensures, e.g., the specific location of transcription and/or translation of the nucleic acid molecule of the invention in a specific tissue (e.g., endosperm, leaf, stem, tuber, meristem, fruit, root, seed) or cell compartment (e.g., cytosol, apoplast, plastid, mitochondrium, vacuole, lysosome). Optionally, the term "regulatory element" comprises also nucleic acid molecules which ensures, e.g., timely limited transcription and/or translation of the nucleic acid molecule of the invention. Furthermore, the "regulatory element" may optionally be chemically triggered.

The introduction of a nucleic acid molecule of the invention into a plant cell, preferably a DNA or RNA molecule, is generally carried out using cloning vectors which ensure stable integration of the nucleic acid molecule into the plant genome. In order to introduce a nucleic acid molecule into a higher plant a large number of cloning vectors are available containing a replication signal for *E. coli* and a marker gene for the selection of transformed bacterial cells, e.g., pBR322, pUC series, M13 mp series, pACYC184. The nucleic acid molecule of the invention may be integrated into the vector at a suitable restriction site by use of one or more restriction endonuclease enzymes. The obtained plasmid is used for the transformation of, e.g., *E. coli* cells. Transformed cells are cultivated in a suitable medium and subsequently harvested and lysed, the plasmid DNA is recovered by means of standard methods and is generally analyzed by restriction and/or sequence analysis. After each manipulation the plasmid DNA may be cleaved and the obtained DNA fragments linked to other DNA sequences. In order to introduce DNA into a plant host cell a wide range of transformation methods and techniques are available, e.g., T-DNA transformation by use of *Agrobacterium tumefaciens* or *Agrobacterium rhizogenes*, fusion of protoplasts, injection of DNA, electroporation of DNA, and the introduction of DNA by membrane permeation (PEG) or means of the biolistic method and others. If whole plants are to be regenerated from transgenic plant cells, a selectable marker gene should be present. If the Ti- or Ri-plasmid is used, e.g., for transformation of the plant cell, at least the right border, preferably, the right and left border of the Ti- and Ri-plasmid T-DNA should be linked with the polynucleotide to be introduced into the plant cell as a flanking region. If Agrobacteria are used for transformation, the DNA to be introduced should be cloned into either an intermediate vector or binary vector. Due to sequence homologies to the sequences of the T-DNA, the intermediate vectors may be integrated into the Ti- or Ri-plasmid of the *Agrobacterium* by homologous recombination. Said intermediate vectors also contain the vir-region necessary for the transfer of the T-DNA. Since intermediate vectors cannot replicate in Agrobacteria, a helper plasmid may transfer the intermediate vector to *Agrobacterium* (conjugation). Binary vectors may replicate in *E. coli* and in Agrobacteria. They contain a selectable marker gene and a linker or polylinker which is flanked by the right and the left T-DNA border region. They may be transformed directly into the Agrobacteria (Holsters et al.

Mol. Gen. Genet. 163 (1978), 181–187). The plasmids used for the transformation of Agrobacteria further comprise a selectable marker gene, e.g., the NPT II gene which allows for the selection of the transformed bacteria. The plasmid may comprise further selection marker genes e.g. conferring resistance against spectinomycin (Svab et al., Proc. Natl. Acad. Sci. U.S.A. 87 (1990), 8526–8530; Sval et al., Plant. Mol. Biol. 14 (1990), 197–206), streptomycin (Jones et al., Mol. Gen. Genet. 91 (1987), 86–91; Svab et al., Proc. Natl. Acad. Sci. U.S.A. 87 (1990), 8526–8530; Svab et al., Plant. Mol. Biol. 14 (1990), 197–206), phosphinothricine (De Block et al., EMBO J. 6 (1987), 2513–2518), glyphosate (Thompson et al., EMBO J. 6 (1987), 2519–2523; Thompson et al., Weed Sci. 35 (1987), 19–23 (suppl.)), or hygromycin (Waldron et al., Plant Mol. Biol. 5 (1985), 103–108). The *Agrobacterium* host cell should contain a plasmid carrying a vir-region. The vir-region is necessary for the transfer of the T-DNA into the plant cell. Additional T-DNA may be present. The transformed *Agrobacterium* is further used for the transformation of plant cells.

The use of T-DNA for the transformation of plant cells is described in EP-A-120 516; Hoekema, In: The Binary Plant Vector System Offestdrukkerij Kanters B. V., Alblasserdam (1985), Chapter V; Fraley et al., Crit. Rev. Plant Sci., 4, 1–46 and An et al., EMBO J. 4 (1985), 277–287. Binary vectors are commercially available, e.g., pBIN19 (Clontech Laboratories, Inc., USA).

For transferring the DNA into the plant cells, plant explants may be co-cultivated with *Agrobacterium tumefaciens* or *Agrobacterium rhizogenes*. Whole plants may be regenerated from infected plant material (e.g., pieces of leaves, stem segments, roots, but also protoplasts or suspension-cultivated plant cells) in a suitable medium which allows for the selection of transformed cells (e.g., containing antibiotics or biocides etc.). The obtained plants are screened for the presence of the introduced DNA. Other possibilities in order to introduce foreign DNA by using, e.g., the biolistic method or by transforming protoplasts are known to the skilled person (e.g., Wilimitzer, L., 1993 Transgenic plants. In Biotechnology, A Multi-Volume Comprehensive Treatise (H. J. Rehm, G. Reed, A. Pühler, P. Stadler, eds.), Vol. 2, 627–659, VCH Weinheim-New York-Basel-Cambridge).

The transformation of dicotyledonous plants by Ti-plasmid-vector systems by means of *Agrobacterium tumefaciens* is a well-established method. Agrobacteria can also be used for the transformation of monocotyledonous plants (Chan et al., Plant Mol. Biol. 22 (1993), 491–506; Hiei et al., Plant J. 6 (1994), 271–282).

Alternative methods for the transformation of monocotyledonous plants are, e.g., the transformation by means of the biolistic approach, protoplast transformation, electroporation of partially permeabilized cells, the introduction of DNA by means of glass fibers. Various references refer to the transformation of maize (WO 95/06128-A1, EP-A-0 513 849; EP-A-0 465 875). EP-A-292 435 describes a method how to obtain fertile plants starting from mucousless, friable granulous maize callus. Shillito et al. (Bio/Technology 7 (1989), 581) started from callus-suspension cultures which produce dividing protoplasts which are capable to regenerate to whole plants.

With regard to the transformation of wheat various methods can be applied, e.g., *agrobacterium*-medicated gene transfer (Hiei et al., Plant J. 6 (1994), 271–282; Hiei et al., Plant Mol. Biol. 35 (1997), 205–218; Park et al., J. Plant Biol. 38 (1995), 365–371), protoplast transformation (Data in "Gene transfer to plants", I. Potrykus, G. Spangenberg (Eds.), Springer-Verlag Berlin Heidelberg, 1995, pages 66–75; Datta et al., Plant Mol. Biol. 20 (1992), 619–629; Sadasivam et al., Plant Cell Rep. (1994), 394–396) the biolistic approach (Li et al., Plant Cell Rep. 12 (1993), 250–255; Cao et al., Plant Cell Rep. 11 (1992), 586–591; Christou, Plant Mol. Biol. 81997), 197–203) and electroporation (Xu et al., in "Gene transfer to plants", I. Potrykus, G. Spangenberg (Bds.), Springer-Verlag Berlin Heidelberg (1995), 201–208).

Once the introduced DNA has been integrated in the genome of the plant cell, it is usually stably integrated and remains within the genome of the descendants of the originally transformed cell. Usually the transformed cell contains a selectable marker gene which allows for the selections of the transformands in the presence of certain sugars, amino acids, biocids or antibiotics, e.g., kanamycin, G 428, bleomycin, hygromycin or phosphinothricine. Therefore, an individual marker gene allows for the selection of the transformed cells against cells lacking the introduced DNA.

After selection the transformed cells are cultivated under normal conditions and grow to a whole plant (McCormick et al., Plant Cell Reports 5 (1986), 81–84). The resulting plants can be cross-bred with plants having the same transformed genetic heritage or a different genetic heritage. Resulting individuals or hybrids have the corresponding phenotypic properties. Two or more generations should be grown in order to ensure whether the phenotypic feature is stable and transferable. Furthermore, seeds should be harvested in order to ensure that the corresponding phenotype or other properties will remain.

The modified starch obtainable from the plant cells, from the plants of the invention, or obtainable by the process of the invention is suitable for numerous industrial applications. Basically, starch can be subdivided into two major fields. One field comprises the hydrolysis products of starch, another the so-called native starches. The hydrolysis essentially comprise glucose and glucane components obtained by enzymatic or chemical processes. They can be used for further processes, such as fermentations and chemical modifications. Currently, starch hydrolysis is carried out substantially enzymatically using amyloglucosidase. Costs might be reduced by using lower amounts of enzyme for hydrolysis due to changes in the starch structure, e.g., increasing the surface of the grain, improved digestibility due to less branching or an altered steric structure, which limits the accesibility for the used enzymes. The use of the so-called native starch can be subdivided into the following areas:

(a) Use for the Preparation of Foodstuffs

Starch is a classic additive for various foodstuffs, wherein it essentially serves the purpose of binding aqueous additives and/or causes an increased viscositiy or an increased gel formation. Important characteristic properties are flowing and sorption behaviour, swelling and pastification temperature, viscositiy and thickening performance, solubility of the starch, transparency and paste structure, heat, shear and acid resistance, tendency to retrogradation, capability of film formation, resistance of freezing/thawing, digestibility as well as the capability of complex formation with, e.g., inorganic or organic ions.

(b) Use for the Preparation of Non-foodstuffs

The other major field of application is the use of starch as an adjuvant in various production processes or as an additive in technical products. The major fields of application for the use of starch as an adjuvant are, first of all, the paper and cardboard industry. In this field, the starch is mainly and for retention (holding back solids), for sizing filler and fine particles, as solidifying substance and for dehydration. In addition, the advantageous properties of starch with regard to stiffness, hardness, sound, grip, gloss, smoothness, tear strength as well as the surfaces are utilized.

Within the paper production process, a differentiation can be made between four fields of application, namely surface, coating, mass and spraying.

The requirement on starch with regard to surface treatment are essentially a high degree of brightness, corresponding viscosity, high viscosity stability, good film formation as well as low formation of dust. When used in coating the solid content, a corresponding viscosity, a high capability to bind as well as high pigment affinity play an important role. As an additive to the mass rapid, uniform, loss-free dispersion, high mechanical stability and complete retention in the paper pulp are of importance. When using the starch in spraying, corresponding content of solids, high viscosity as well as high capability to bind are also significant. A major field of application is, for instance, in the adhesive industry, where the fields of application are subdivided into four areas: the use of pure starch glue, the use in starch glues prepared with special chemicals, the use of starch as an additive to synthetic resins and polymer dispersions as well as the use of starches as extenders for synthetic adhesives. 90% of all starch-based adhesives are used in the production of corrugated board, paper sacks and bags, composits materials for paper and aluminum, boxes and wetting glue for envelopes, stamps, etc.

Another possible use as adjuvant and additive is in the production of textiles care products. Within the textile industry, a differentiation can be made between the following four fields of application: the use of starch as a sizing agent, i.e. as an adjuvant for smoothing and strengthening the burring behaviour for the protection against tensile forces active in weaving as well as for the increase of wear resistance during weaving as an agent for textile improvement mainly after quality-deteriorating pretreatments, such as bleaching dying, etc., as thickener in the production of dye pastes for the prevention of dye diffusion and as an additive for warping agents for sewing yarns.

Furthermore starch may be used as an additive in building materials. One example is the production of gypsum plaster boards, wherein the starch mixed in the thin plaster pastifies with the water, diffuses at the surface of the gypsum board and thus binds the cardboard to the board. Other fields of application are admixing it to plaster and mineral fibers. In ready-mixed concrete, starch may be used for the deceleration of the sizing process.

Furthermore, the starch is advantageous for the production of means for ground stabilization used for the temporary protection of ground particles against water in artificial earth shifting. According to state-of-the-art knowledge, combination products consisting of starch and polymer emulsions can be considered to have the same erosion- and encrustation-reducing effect as the products used so far; however, they are considerably less expensive.

Another field of application is the use of starch in plant protectives for the modification of the specific properties of these preparations. For instance, starches are used for improving the wetting of plant protective and fertilisers, for the dosed release of the active ingredients, for the conversion of liquid, volatile and/or odorous active ingredients into microcristalline, stable, deformable substances, for mixing incompatible compositions and for the prolongation of the duration of the effect due to a reduced disintegration.

Starch may also be used in the fields of drugs, medicine and in the cosmetics industry. In the pharmaceutical industry, the starch may be used as a binder for tablets or for the dilution of the binder in capsules. Furthermore, starch is suitable as disintegrant for tablets since, upon swallowing, it absorbs fluid and after a short time it swells so much that the active ingredient is released. It is also a suitable auxiliary to achieve a time-delayed release of the active ingredient (retardation effect). For qualitative reasons, medicinal flowance and dusting powders are further fields of application. In the field of cosmetics, the starch may for example be used as a carrier of powder additives, such as scents and salicylic acid. A relatively extensive field of application for the starch is toothpaste.

The use of starch as an additive in coal and briquettes is also suitable. By adding starch, coal can be quantitatively agglomerated and/or briquetted in high quality, thus preventing premature disintegration of the briquettes. Barbecue coal contains between 4 and 6% added starch, calorated coal between 0.1 and 0.5%. Furthermore, the starch is suitable as a binding agent since adding it to coal and briquette can considerably reduce the emission of toxic substances.

Furthermore, the starch may be used as a flocculent in the processing of ore and coal slurry.

Another field of application is the use as an additive to process materials in casting. For various casting processes cores produced from sands mixed with binding agents are needed. Nowadays, the most commonly used binding agent is bentonite mixed with modified starches, mostly swelling starches.

The purposes of adding starch is increased flow resistance as well as improved binding strength. Moreover, swelling starches may fulfill more prerequisites for the production process, such as dispersability in cold water, rehydratisability, good mixability in sand and high capability of binding water.

In the rubber industry starch may be used for improving the technical and optical quality. Reasons for this are improved surface gloss, grip and appearance. For this purpose, the starch is dispersed on the stickly rubberized surfaces of rubber substances before the cold vulcanization. It may also be used for improving the printability of rubber.

Another field of application for the modified starch is the production of leather substitutes.

In the plastics market the following fields of application are emerging: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talcum. This situation is different when the specific starch properties become effective and the property profile of the end products is thus clearly changed. One example is the use of starch products in the processing of thermoplastic materials, such as polyethylene. Thereby, starch and the synthetic polymer are combined in a ratio of 1:1 by means of coexpression to form a master batch, from which various products are produced by means of common techniques using granulated polyethylene. The integration of starch in polyethylene films may cause an increased substance permeability in hollow bodies, improved water vapor permeability, improved antistatic behaviour, improvied antiblock behaviour as well as improved printability with aqueous dyes.

Another possibility is the use of the starch in polyurethane foams. Due to the adaption of starch derivatives as well as due to the optimization of processing techniques, it is possible to specifically control the reaction between synthetic polymers and the starch's hydroxy groups. The results are polyurethane films having the following property profiles due to the use of starch: a reduced coefficient of thermal expansion, decreased shrinking behaviour, improved pressure/tension behaviour, increased water vapor permeability without a change in water acceptance, reduced flammability and cracking density, no drop off of combustible parts, no halides and reduced aging. Disadvantages that presently still exists are reduced pressure and impact strength.

Product development of film is not the only option. Also solid plastics products, such as pots, plates and bowls can be produced by means of a starch content of more than 50%. Furthermore, the starch/polymer mixtures offer the advantage that they are much easier biodegradable.

Furthermore, due to their extreme capability to bind water, starch graft polymers have gained utmost importance. These are products having a backbone of starch and a side lattice of a synthetic monomer grafted on according to the principle of radical chain mechanism. The starch graft polymers available nowadays are characterized by an improved binding and retaining capability of up to 1000 g water per g starch at a high viscosity. These super absorbers are used mainly in the hygiene field, e.g., in products such as diapers and sheets, as well as in the agricultural sector, e.g., in seed pellets.

Deposit of Biological Material

The following plasmids as described in the present invention were deposited in accordance with the requirements of the Budapest Treaty at the Deutsche Sammlung fur Mikroorganismen und Zellkulturen (DSMZ) in Braunschweig, Germany: Plasmid pTaR1-11 refers to accession number DSM No. 12810 at May 20, 1999. Plasmid RS26-88 refers to accession number DSM No. 13511 at May 24, 2000.

EXAMPLES

The following Examples shall merely illustrate the invention and do not limit the invention in any way.

Example 1

Preparation of a cDNA from *Triticum aestivum L.*, cv Florida encoding R1-protein For identification and isolation of a cDNA encoding R1-protein derived from wheat a wheat cDNA library was prepared from poly(A)+ RNA of a 21 day old caryopsis ("starchy"-endosperm) of wheat plants by use of lambda zap II vector (Lambda ZAP II-cDNA Synthesis Kit, Stratagene GmbH, Heidelberg, Germany) according to the manufacterer's protocoll. The primary titer of the cDNA library was about 1,26×10$^6$ pfu/ml.

Screening of the cDNA library was performed using the oligonucleotides R1A and R1B as primers for PCR (polymerase chain reaction) amplification of a DNA insert of plasmid pBinAR Hyg (DSM 9505) containing a cDNA encoding R1-protein derived from maize. Said plasmid is, e.g., obtainable according to Example 14 of WO 98/27212. Therefore, the disclosure content of WO 98/27212-A1 is expressly incorporated herein by reference.

After Xba I/Asp 718 restricton endonuclease digestion of vector pBluescript, a cDNA fragment was purified by agarose gel electrophoresis and standard protocolls.

As a template for the PCR-amplification of said maize cDNA fragment, about 10 pg of the above isolated maize cDNA fragment were used.

The PCR buffer contained 1.5 mM MgCl$_2$, 20 mM Tris-HCL (pH 8.4), 50 mM KCl, 0.8 mM dNTP mix, 1 µM primer R1A, 1 µM primer R1B und 2.5 units Taq polymerase.

R1A: 5' TATTGGAAGCTCGAGTTGAAC 3'  (Seq. ID No.3)

R1B: 5' TTGAGCTGTCTAATAGATGCA 3'  (Seq. ID No.4)

PCR cycling was performed in a Trioblock® PCR-thermocycler (Biometra, Germany) according to the following protocoll: 4' at 95° C.; 1' at 96° C.; 45" at 62° C.; 1'15" at 72° C.; 30 cycles and 5' at 72° C. in order to amplify a cDNA fragment encoding R1-protein derived from maize.

Subsequently, the obtained fragment was random-primed digoxygenin-labelled according to the manufacturers protocoll (Boehringer Mannheim, The DIG system users Guide).

The amplified and labelled cDNA fragment of 1924 bp was further used as a heterologous probe for the screening of the above prepared cDNA library derived from wheat.

About 3.5×10$^5$ phages were screened according to standard protocolls.

After pre-hybridization in 5×SSC, 3% Blocking (Boehringer Mannheim), 0.2% SDS, 0.1% sodium laurylsarcosine and 50 µg/ml herring sperm DNA at 55° C., the filters were hybridized overnight with 1 ng/ml of the digoxigenin labeled (Random Primed DNA Labeling Kit) r1-protein probe (the 1924 bp XbaI/Asp718 cDNA fragment of maize). The filters were washed 2 times for 5' with 2×SSC, 1% SDS at room temperature; 2 times for 10' with 1×SSC, 0.5% SDS at 55° C., and 2 times for 10' in 0.5× SSC, 0.2% SDS at 55° C.

Positive clones were rescreened and purified. The plasmids (pBluescript SK Phagemide) were isolated by in vivo excision, according to the manufacterer's protocol (Stratagene, Heidelberg). After characterization of the clones by restriction analysis, the longest cDNA inserts were further analyzed.

Example 2

Sequence analysis of cDNA insert of pTaR1-11

The nucleotide sequence of the isolated cDNA insert of clone pTaR1-11 was analyzed according to the dideoxynucleotide method (Sanger et al., Proc. Natl. Acad. Sci. USA 74 (1977), 5463–5467).

Clone TaR1-11 contains a 672 bp insert representing a partial cDNA according to Seq. ID No. 1 encoding R1-protein according to Seq. ID No. 2 derived from wheat.

The corresponding amino acid sequence of the polynucleotide of Seq ID No. 1 is given in Seq. ID. No. 2.

Example 3

Isolation and sequence identification of a cDNA from *Triticum aestivum L.*cv Florida encoding R1-protein For identification and isolation of a cDNA encoding the R1-protein from wheat poly(A+)-RNA was isolated from 3–6 weeks old leaves from wheat and reverse transcripted using RT-PCR-Kit (Titan One tube RT-PCR System, Roche Diagnostics, Mannheim, Germany) according to the manufacter's protocol. Amplification of a cDNA encoding the R1-protein was performed using oligo-nucleotides Zm-R1-2 (Seq ID No. 5) and Wh-R1-5 (Seq ID No. 6) and an aliquot of RT-reaction as template.

The following primers were selected as hybridisation probe for the isolation of the desired DNA encoding R1 protein: The primer binding sites are localized in Seq. ID no's. 7 and 9 at position 1–24 and 3402–3418):

```
Zm-R1-2:
5'- CTG TGG TAT GTC TGG AC-3'          (Seq ID No.5)

Wh-R1-5':
5'-GAG GAA GCA AGG AAG GAA CTG CAG-3'  (Seq ID No.6)
```

The PCR-reaction was performed in an Eppendorf Mastercycler™ gradient (Eppendorf, Hamburg, Germany) and contained 10 mM Tris-HCl pH 8,85, 25 mM KCl, 5 mM $(NH_4)_2SO_4$, 1,5 mM $MgSO_4$, 0,8 mM dNTPs, 1 µM Primer Zm-R1-2, 1 µM Primer Wh-R1-5 and 1 Unit Pwo-DNA-Polymerase. The following temperature program was proceeded:

Initially 2' at 94° C., then 35 cycles of 1' 94° C., 1' at 55° C. and 3 ' at 72° C. and a final step of 5' at 72° C. The obtained DNA-fragment of 3,4 kb was cloned into the EcoRV-site of a pBluescript SK(–) vector resulting in plasmid RS 23-88 was further analysed for the nucleotide sequence in cooperation with GATC GmbH (Konstanz, Germany) and specified as SEQ ID No. 7 represents the main-part of the R1-gene with ~1 kb of the 5'-end and ~300 bp of the 3'-end lacking. The missing 3'-region was complemented with the corresponding region of a partial R1-cDNA clone as described in example 1 and 2 resulting in plasmid RS 26-88 and comprising SEQ ID No. 9. In order to achieve that the clone RS 23-88 was digested with the restriction endonuclease Ec/136. The resulting large fragment was used for further cloning, whereas the smaller 140 bp fragment was discarded. The clone TaR1-11 from example 1 and 2 which contains the 3'-region of the R1 cDNA from wheat was treated with the restriction endonuclease XhoI, the restriction site was filled up to blunt end using T4-DNA-Polymerase and the 3'-region of the R1 cDNA from wheat was released from the vector by digestion with the restriction endonuclease Ec/136. This produced fragment was ligated to the blunt ends of Ec/136-digested RS 23-88. The orientation of the ligated fragment was controlled by restriction analysis.

The primary structure of the whole cDNA clone (~3,7 kb) was again determined by sequence analysis performed by GATC GmbH (Konstanz, Germany) and specified as SEQ ID No. 9.

The invention claimed is:

1. A wheat cell transformed with a DNA molecule consisting of:
   an isolated DNA molecule selected from the group consisting of SEQ ID NO: 1 and SEQ ID NO: 9,
   wherein the presence of the DNA molecule leads to inhibition of expression of at least one endogenous gene encoding an R1 protein.

2. The wheat cell of claim 1, wherein the DNA molecule is transcribed into antisense RNA, which leads to the inhibition of expression of at least one endogenous gene encoding an R1 protein.

3. The wheat cell of claim 1, wherein the DNA molecule is transcribed into a cosuppression RNA, which leads to the inhibition of expression of at least one endogenous gene encoding an R1 protein.

4. The wheat cell of claim 2, wherein said DNA molecule is linked in antisense orientation with one or more regulatory elements ensuring the transcription and/or translation in said cell.

5. A transgenic plant comprising the wheat cell of claim 1, wherein the plant is a wheat plant.

6. Propagation material from the plant of claim 5.

7. A seed from the transgenic plant of claim 5, wherein the seed comprises said wheat cell.

8. A process for producing modified starch comprising extracting modified starch from the plant of claim 5 or from parts thereof.

9. A wheat cell transformed with a DNA molecule consisting of an isolated DNA molecule encoding the polypeptide of SEQ ID NO: 2 or SEQ ID NO: 10, wherein said DNA molecule contains a sequence with a homology of over 90% to the nucleic acid sequence of SEQ ID NO: 1 or SEQ ID NO: 9, and wherein the presence of said DNA molecule leads to inhibition of expression of at least one endogenous gene encoding an R1 protein.

10. The wheat cell of claim 9, wherein said DNA molecule contains a sequence with the homology of over 95% to a nucleic acid sequence of SEQ ID NO: 1 or SEQ ID NO: 9.

* * * * *